(12) United States Patent
Rondeau et al.

(10) Patent No.: US 7,507,260 B2
(45) Date of Patent: Mar. 24, 2009

(54) COMPOSITION FOR DYEING KERATINOUS FIBRES WITH A CATIONIC DIRECT DYE AND A SILICONE

(75) Inventors: Christine Rondeau, Sartrouville (FR); Gérard Lang, Saint Prix (FR); Jean Cotteret, Verneuil sur Seine (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 11/539,459

(22) Filed: Oct. 6, 2006

(65) Prior Publication Data

US 2007/0261178 A1 Nov. 15, 2007

Related U.S. Application Data

(63) Continuation of application No. 10/840,953, filed on May 7, 2004, now abandoned, which is a continuation of application No. 09/530,198, filed as application No. PCT/FR99/01876 on Jul. 29, 1999, now abandoned.

(51) Int. Cl.
*A61Q 5/10* (2006.01)
(52) U.S. Cl. .................. 8/405; 8/406; 8/408; 8/426; 8/554; 8/581
(58) Field of Classification Search ............ 8/405, 8/406, 408, 426, 554, 581
See application file for complete search history.

(56) References Cited

U.S. PATENT DOCUMENTS

| | | | |
|---|---|---|---|
| 3,869,454 A | 3/1975 | Lang et al. | |
| 3,955,918 A | 5/1976 | Lang | |
| 3,985,499 A | 10/1976 | Lang et al. | |
| 4,025,301 A | 5/1977 | Lang | |
| 4,153,065 A | 5/1979 | Lang | |
| 4,185,087 A | 1/1980 | Morlino | |
| 4,820,308 A | 4/1989 | Madrange et al. | |
| 4,823,985 A | 4/1989 | Grollier et al. | |
| 4,898,595 A | 2/1990 | Fridd et al. | |
| 5,070,171 A | 12/1991 | O'Lenick, Jr. | |
| 5,091,493 A | 2/1992 | O'Lenick, Jr. et al. | |
| 5,093,452 A | 3/1992 | O'Lenick, Jr. | |
| 5,143,518 A * | 9/1992 | Madrange et al. | 8/405 |
| 5,149,765 A | 9/1992 | O'Lenick, Jr. | |
| 5,708,151 A | 1/1998 | Möckli | |
| 5,888,252 A | 3/1999 | Möckli | |
| 5,980,587 A | 11/1999 | Samain | |
| 5,993,490 A | 11/1999 | Rondeau et al. | |
| 6,001,135 A * | 12/1999 | Rondeau et al. | 8/407 |
| 6,364,913 B1 | 4/2002 | Hurschmann et al. | |
| 6,368,360 B2 | 4/2002 | Samain | |

FOREIGN PATENT DOCUMENTS

| | | |
|---|---|---|
| DE | 35 36 406 A1 | 4/1986 |
| DE | 37 06 053 A1 | 8/1987 |
| DE | 196 41 841 C1 | 10/1997 |
| DE | 196 19 071 A1 | 11/1997 |
| DE | 197 13 696 C1 | 6/1998 |
| DE | 197 13 697 C1 | 6/1998 |
| EP | 0 095 238 | 11/1983 |
| EP | 0 429 855 A1 | 6/1991 |
| EP | 0 470 381 A2 | 2/1992 |
| EP | 0 492 657 | 7/1992 |
| EP | 0 503 507 A1 | 9/1992 |
| EP | 0 714 954 | 6/1996 |
| EP | 0 756 861 A2 | 2/1997 |
| EP | 0 850 637 | 7/1998 |
| EP | 0 850 638 | 7/1998 |
| FR | 2 140 205 | 1/1973 |
| FR | 2 189 006 | 1/1974 |
| FR | 2 282 860 | 3/1976 |
| FR | 2 285 851 | 4/1976 |
| FR | 2 586 913 | 3/1987 |
| GB | 2 138 845 A | 10/1984 |
| GB | 2 173 515 A | 4/1985 |
| GB | 2 168 082 | 6/1986 |
| GB | 2 168 082 A | 6/1986 |
| GB | 2 173 515 | 10/1986 |
| JP | 57-192310 | 11/1982 |
| JP | 62-209015 | 9/1987 |
| JP | 4-334313 | 11/1992 |
| JP | 8-507545 | 8/1996 |
| JP | 10-502946 | 3/1998 |
| JP | 10-182379 | 7/1998 |
| WO | WO 95/01772 | 1/1995 |
| WO | WO 95/15144 | 6/1995 |
| WO | WO 97/20545 | 6/1997 |

OTHER PUBLICATIONS

ANOM. "Arbeitsbericht Versuche zum Einfluss aminierter Silikone auf die Haafärbeelgenschaften kationischer Direktfarbstoffe," Nov. 8, 2005, Institute Dr. Schrader.
English Language Derwent Abstract of DE 196 41 841 C1, 1997.
English Language Derwent Abstract of DE 197 13 696 C1, 1998.

(Continued)

*Primary Examiner*—Eisa B Elhilo
(74) *Attorney, Agent, or Firm*—Finnegan, Henderson, Farabow, Garrett & Dunner, L.L.P.

(57) ABSTRACT

The invention relates to a composition for dyeing keratinous fibers, in particular human keratinous fibers such as hair, comprising, in an appropriate dyeing medium, at least one cationic direct dye of a given formula, and which is characterized in that it contains, in addition, at least one silicone chosen from the aminated silicones, the polyoxyalkylenated silicones, the silicone gums and resins. The invention also relates to the dyeing methods and devices using it.

62 Claims, No Drawings

OTHER PUBLICATIONS

English Language Derwent Abstract of DE 197 13 697 C1, 1998.
English Language Derwent Abstract of JP 4-334313, 1992.
English Language Derwent Abstract of JP 57-192310, 1982.

Schrader, K. "Grundlagen und Rezepturen der Kosmetika," 1989, 812-815.

* cited by examiner

COMPOSITION FOR DYEING KERATINOUS FIBRES WITH A CATIONIC DIRECT DYE AND A SILICONE

CROSS-REFERENCE TO RELATED APPLICATIONS

This application is a continuation of the U.S. application Ser. No. 10/840,953, filed on May 7, 2004, and abandoned on Oct. 23, 2006, which is a continuation of application Ser. No. 09/530,198, filed Jun. 21, 2000, and abandoned on May 27, 2004, which is a national stage application of International application No. PCT/FR 99/01876, filed Jul. 29, 1999, and for which the national stage was entered on Apr. 26, 2000, and the requirements under 35 U.S.C. §371 were met on Jun. 21, 2000, all of which are incorporated herein by reference.

FIELD OF THE INVENTION

The invention relates to a composition for dyeing keratinous fibres, in particular human keratinous fibres such as hair, comprising, in an appropriate dyeing medium, at least one cationic direct dye of a given formula, and at least one particular silicone.

The subject of the invention is also the dyeing methods and devices using the said composition.

BACKGROUND OF THE INVENTION

In the hair domain, it is possible to distinguish two types of dyeing.

The first is the semipermanent or temporary dyeing, or direct dyeing, which involves dyes capable of bringing the natural colour of the hair a more or less marked colour modification which is resistant, where appropriate, to several shampooings. These dyes are called direct dyes; they can be used with or without oxidizing agent. In the presence of oxidizing agent, the aim is to obtain a lightening dyeing. Lightening dyeing is performed by applying to the hair the fresh mixture of a direct dye and of an oxidizing agent and makes it possible in particular to obtain, by lightening of the melanine of the hair, an advantageous effect such as a uniform colour in the case of grey hair or to make the colour stand out in the case of naturally pigmented hair.

The second is permanent dyeing or oxidation dyeing. The latter is performed with so-called "oxidation" dyes comprising oxidation dye precursors and couplers. The oxidation dye precursors, commonly called "oxidation bases" are compounds which are initially colourless or faintly coloured which develop their dyeing power inside the hair in the presence of oxidizing agents added at the time of use, leading to the formation of coloured and dyeing compounds. The formation of these coloured and dyeing compounds results either from an oxidative condensation of the "oxidation bases" with themselves, or an oxidative condensation of the "oxidation bases" with colour modifying compounds commonly called "couplers" and generally present in the dyeing compositions used in oxidation dyeing.

To vary the shades obtained with the said oxidation dyes, or to increase their shimmer, direct dyes are sometimes added to them.

Among the cationic direct dyes available in the field of dyeing of keratinous fibres, especially human keratinous fibres, compounds are already known whose structure is developed in the text which follows; nevertheless, these dyes lead to colours which exhibit characteristics which are still inadequate from the point of view of the intensity and homogeneity of the colour distributed along the fibre; it is said, in this case, that the colour is too selective, and from the point of view of fastness, in terms of resistance to various attacks to which the hair may be subjected (light, adverse weather conditions, shampooings).

SUMMARY OF THE INVENTION

However, after major research studies carried out on this question, the applicant has just now discovered that it is possible to obtain novel compositions for dyeing keratinous fibres which are capable of giving intense and nevertheless only slightly selective colours which are quite resistant to the various attacks to which the hair may be subjected, by combining at least one particular silicone with at least one cationic direct dye known in the prior art and which have the respective formulae defined hereinafter.

This discovery forms the basis of the present invention.

DETAILED DESCRIPTION OF THE INVENTION

The first subject of the present invention is therefore a composition for dyeing keratinous fibres and in particular human keratinous fibres such as hair, containing in an appropriate dyeing medium, (i) at least one cationic direct dye whose structure corresponds to the formulae (I) to (IV) defined hereinafter, characterized in that it contains in addition (ii) at least one particular silicone.

(i) The cationic direct dye which can be used according to the present invention is a compound chosen from those of the following formulae (I), (II), (III), (III'), (IV):

a) the compounds of the following formula (I):

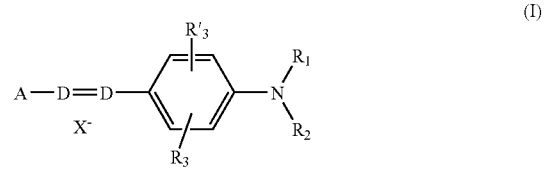

in which:

D represents a nitrogen atom or the —CH group, $R_1$ and $R_2$, which are identical or different, represent a hydrogen atom; a $C_1$-$C_4$ alkyl radical which may be substituted with a —CN, —OH or —NH$_2$ radical or form with a carbon atom of the benzene ring an optionally oxygen-containing or nitrogen-containing heterocycle which may be substituted with one or more $C_1$-$C_4$ alkyl radicals; a 4'-aminophenyl radical, $R_3$ and $R'_3$, which are identical or different, represent a hydrogen or halogen atom chosen from chlorine, bromine, iodine and fluorine, a cyano, $C_1$-$C_4$ alkyl, $C_1$-$C_4$ alkoxy or acetyloxy radical, $X^-$ represents an anion which is preferably chosen from chloride, methylsulphate and acetate, A represents a group chosen from the following structures $A_1$ to $A_{19}$:
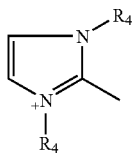
$A_1$
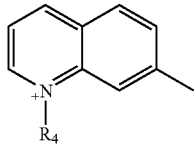
$A_2$
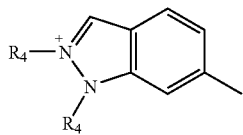
$A_3$
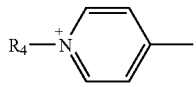
$A_4$
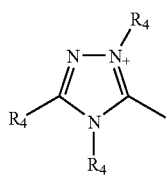
$A_5$
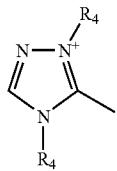
$A_6$
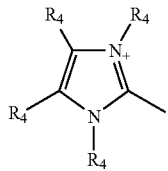
$A_7$
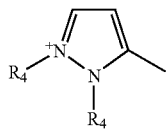
$A_8$
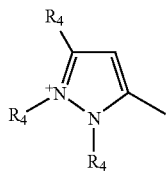
$A_9$
-continued
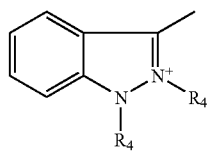
$A_{10}$
$A_{11}$
$A_{12}$
$A_{13}$
$A_{14}$
$A_{15}$
$A_{16}$
$A_{17}$
$A_{18}$
and
$A_{19}$
in which $R_4$ represents a $C_1$-$C_4$ alkyl radical which may be substituted with a hydroxyl radical and $R_5$ represents a $C_1$-$C_4$ alkoxy radical, with the proviso that when D represents —CH, A represents $A_4$ or $A_{13}$ and $R_3$ is different from an alkoxy radical, then $R_1$ and $R_2$ do not simultaneously denote a hydrogen atom;

b) the compounds of the following formula (II):

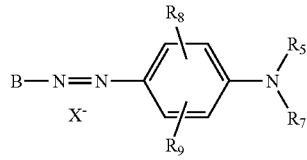
(II)

in which:

$R_6$ represents a hydrogen atom or a $C_1$-$C_4$ alkyl radical, $R_7$ represents a hydrogen atom, an alkyl radical which may be substituted with a —CN radical or with an amino group, a 4'-aminophenyl radical or forms with $R_6$ an optionally oxygen-containing and/or nitrogen-containing heterocycle which may be substituted with a $C_1$-$C_4$ alkyl radical, $R_8$ and $R_9$, which are identical or different, represent a hydrogen atom, a halogen atom such as bromine, chlorine, iodine or fluorine, a $C_1$-$C_4$ alkyl or $C_1$-$C_4$ alkoxy radical, a —CN radical, $X^-$ represents an anion which is preferably chosen from chloride, methylsulphate and acetate, B represents a group chosen from the following structures B1 to B6:

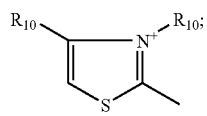
B1

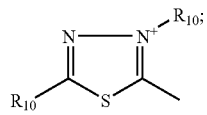
B2

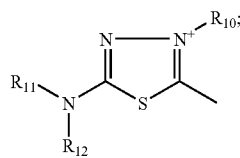
B3

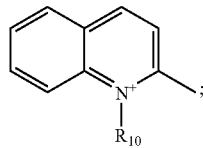
B4

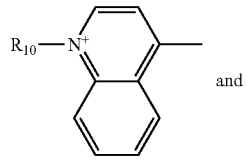
B5 and

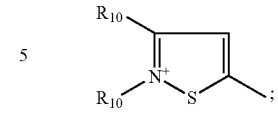
B6 in which $R_{10}$ represents a $C_1$-$C_4$ alkyl radical, $R_{11}$ and $R_{12}$, which are identical or different, represent a hydrogen atom or a $C_1$-$C_4$ alkyl radical;

c) the compounds of the following formulae (III) and (III'):

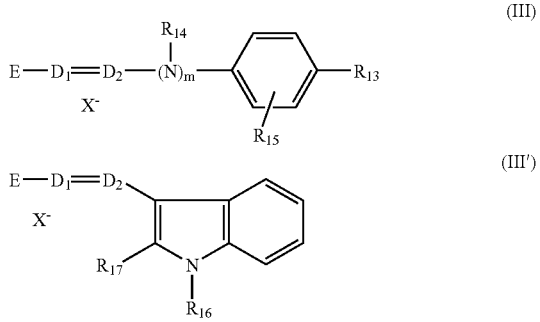

in which:

$R_{13}$ represents a hydrogen atom, a $C_1$-$C_4$ alkoxy radical, a halogen atom such as bromine, chlorine, iodine or fluorine or an amino radical, $R_{14}$ represents a hydrogen atom, a $C_1$-$C_4$ alkyl radical or forms with a carbon atom of the benzene ring a heterocycle which is optionally oxygen-containing and/or substituted with one or more $C_1$-$C_4$ alkyl groups, $R_{15}$ represents a hydrogen or halogen atom such as bromine, chlorine, iodine of fluorine, $R_{16}$ and $R_{17}$, which are identical or different, represent a hydrogen atom or a $C_1$-$C_4$ alkyl radical, $D_1$ and $D_2$, which are identical or different, represent a nitrogen atom or the —CH group, m=0 or 1, it being understood that when $R_{13}$ represents an unsubstituted amino group, then $D_1$ and $D_2$ simultaneously represent a —CH group and m=0, $X^-$ represents an anion which is preferably chosen from chloride, methylsulphate and acetate, E represents a group chosen from the following structures E1 to E8:

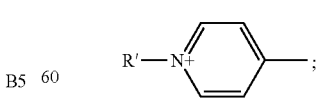
E1

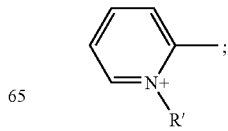
E2

-continued

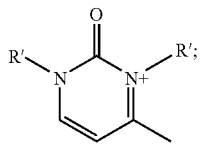

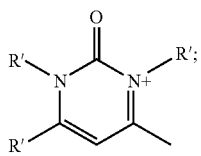

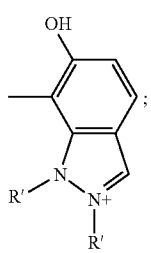

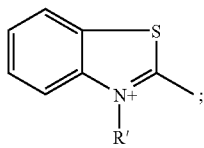

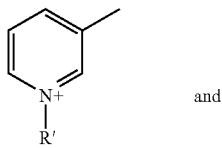

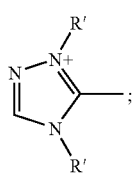

and

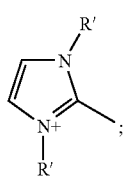

in which R' represents a $C_1$-$C_4$ alkyl radical;

when m=0 and $D_1$ represents a nitrogen atom, then E may also denote a group having the following structure E9:

in which R' represents a $C_1$-$C_4$ alkyl radical, d) the compounds of the following formula (IV):

G—N=N-J  (IV)

in which:

the symbol G represents a group chosen from the following structures $G_1$ to $G_3$:

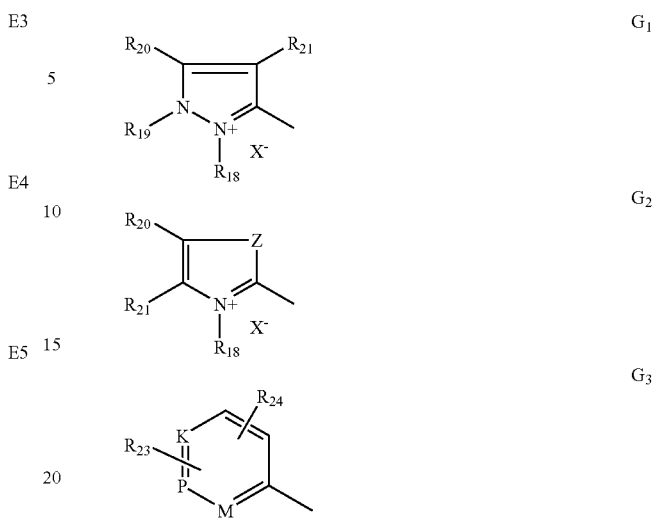

in which structures $G_1$ to $G_3$, $R_{18}$ denotes a $C_1$-$C_4$ alkyl radical, a phenyl radical which may be substituted with a $C_1$-$C_4$ alkyl radical or a halogen atom chosen from chlorine, bromine, iodine and fluorine;

$R_{19}$ denotes a $C_1$-$C_4$ alkyl radical or a phenyl radical;

$R_{20}$ and $R_{21}$, which are identical or different, represent a $C_1$-$C_4$ alkyl radical, a phenyl radical, or form together in $G_1$ a benzene ring which is substituted with one or more $C_1$-$C_4$ alkyl, $C_1$-$C_4$ alkoxy or $NO_2$ radicals, or form together in $G_2$ a benzene ring which is optionally substituted with one or more $C_1$-$C_4$ alkyl, $C_1$-$C_4$ alkoxy or $NO_2$ radicals;

$R_{20}$ may denote, in addition, a hydrogen atom;

Z denotes an oxygen or sulphur atom or an —$NR_{19}$ group;

M represents a group —CH, —CR (R denoting $C_1$-$C_4$ alkyl), or —$NR_{22}(X^-)$;

K represents a group —CH, —CR(R denoting $C_1$-$C_4$ alkyl), or —$NR_{22}(X^-)_r$;

P represents a group —CH, —CR(R denoting $C_1$-$C_4$ alkyl), or —$NR_{22}(X^-)_r$; r denotes zero or 1;

$R_{22}$ represents an $O^-$ atom, a $C_1$-$C_4$ alkoxy radical or a $C_1$-$C_4$ alkyl radical;

$R_{23}$ and $R_{24}$, which are identical or different, represent a hydrogen or halogen atom chosen from chlorine, bromine, iodine and fluorine, a $C_1$-$C_4$ alkyl radical, a $C_1$-$C_4$ alkoxy radical or an —$NO_2$ radical;

$X^-$ represents an anion which is preferably chosen from chloride, iodide, methylsulphate, ethylsulphate, acetate and perchlorate;

with the proviso that if $R_{22}$ denotes $O^-$, then r denotes zero;

if K or P or M denote —N—($C_1$-$C_4$ alkyl)$X^-$, then $R_{23}$ or $R_{24}$ is different from a hydrogen atom;

if K denotes —$NR_{22}(X^-)_r$, then M=P=—CH, —CR;

if M denotes —$NR_{22}(X^-)_r$, then K=P=—CH, —CR;

if P denotes —$NR_{22}(X^-)_r$, then K=M and denote —CH or —CR;

if Z denotes a sulphur atom with $R_2$, denoting $C_1$-$C_4$ alkyl, then $R_{20}$ is different from a hydrogen atom;

if Z denotes —$NR_{22}$ with $R_{19}$ denoting $C_1$-$C_4$ alkyl, then at least one of the $R_{18}$, $R_{20}$ or $R_{21}$ radicals of the group having the structure $G_2$ is different from a $C_1$-$C_4$ alkyl radical;

the symbol J represents:

(a) a group having the following structure $J_1$:

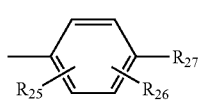

in which structure $J_1$,
R$_{25}$ represents a hydrogen atom, a halogen atom chosen from chlorine, bromine, iodine and fluorine, a $C_1$-$C_4$ alkyl radical, a $C_1$-$C_4$ alkoxy radical, a radical —OH, —NO$_2$, —NHR$_{28}$, —NR$_{29}$R$_{30}$, —NHCO($C_1$-$C_4$alkyl), or forms with R$_{26}$ a 5- or 6-membered ring containing or otherwise one or more heteroatoms chosen from nitrogen, oxygen or sulphur;
R$_{26}$ represents a hydrogen atom, a halogen atom chosen from chlorine, bromine, iodine and fluorine, a $C_1$-$C_4$ alkyl or $C_1$-$C_4$ alkoxy radical, or forms with R$_{27}$ or R$_{28}$ a 5- or 6-membered ring containing or otherwise one or more heteroatoms chosen from nitrogen, oxygen or sulphur;
R$_{27}$ represents a hydrogen atom, an —OH radical, an —NHR$_{28}$ radical, an —NR$_{29}$R$_{30}$ radical;
R$_{28}$ represents a hydrogen atom, a $C_1$-$C_4$ alkyl radical, a $C_1$-$C_4$ monohydroxyalkyl radical, a $C_2$-$C_4$ polyhydroxyalkyl radical, a phenyl radical;
R$_{29}$ and R$_{30}$, which are identical or different, represent a $C_1$-$C_4$ alkyl radical, a $C_1$-$C_4$ monohydroxyalkyl radical, a $C_2$-$C_4$ polyhydroxyalkyl radical;
(b) a 5- or 6-membered nitrogen-containing heterocycle group which is capable of containing other heteroatoms and/or carbonyl-containing groups and which may be substituted with one or more $C_1$-$C_4$ alkyl, amino or phenyl radicals, and in particular a group having the following structure $J_2$:

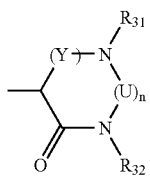

in which structure $J_2$,
R$_{31}$ and R$_{32}$, which are identical or different, represent a hydrogen atom, a $C_1$-$C_4$ alkyl radical, a phenyl radical;
Y denotes the —CO— radical or the radical

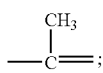

n=0 or 1, with, when n denotes 1, U denotes the —CO— radical.

In the structures (I) to (IV) defined above, the $C_1$-$C_4$ alkyl or alkoxy group preferably denotes methyl, ethyl, butyl, methoxy or ethoxy.

The cationic direct dyes of formulae (I), (II), (III) and (III') which can be used in the dyeing compositions in accordance with the invention are known compounds which are described, for example, in patent applications WO 95/01772, WO 95/15144 and EP-A-0,714,954. Those of formula (IV) which can be used in the dyeing compositions in accordance with the invention are known compounds which are described, for example, in patent applications FR-2,189,006, FR-2,285,851 and FR-2,140,205 and its certificates of addition.

Among the cationic direct dyes of formula (I) which can be used in the dyeing compositions in accordance with the invention, there may be mentioned more particularly the compounds corresponding to the following structures (I1) to (I54):

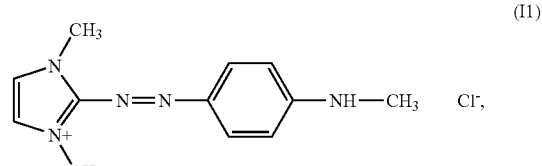
(I1)

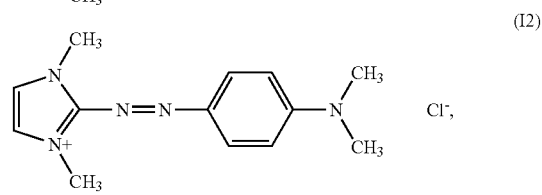
(I2)

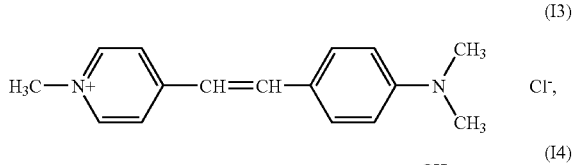
(I3)

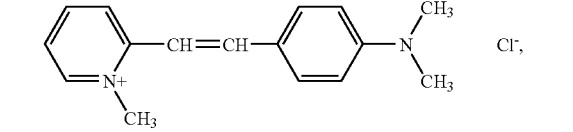
(I4)

(I5)

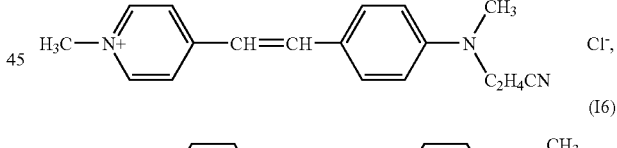
(I6)

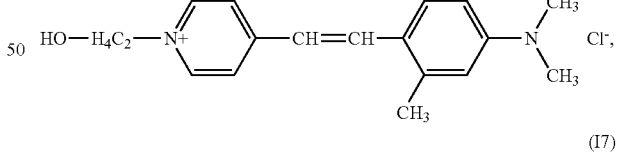
(I7)

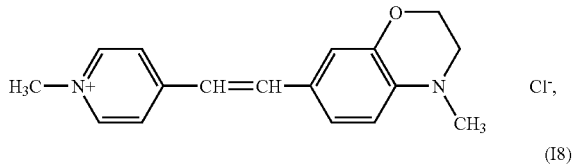
(I7)

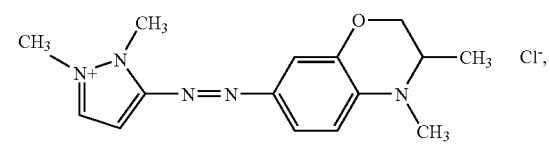
(I8)

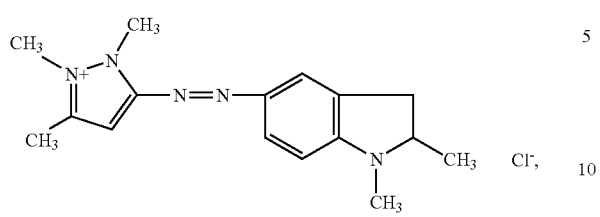 (I9) Cl⁻,
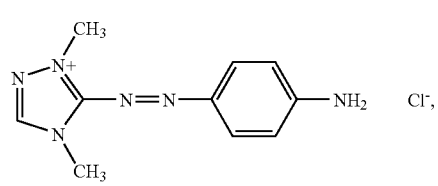 (I10) Cl⁻,
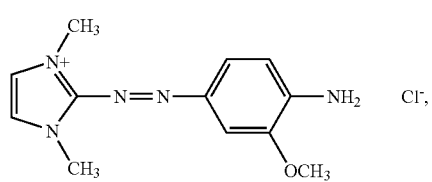 (I11) Cl⁻,
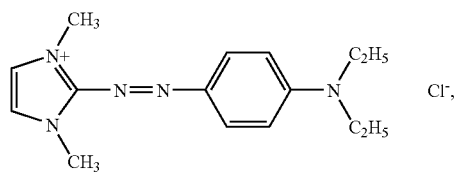 (I12) Cl⁻,
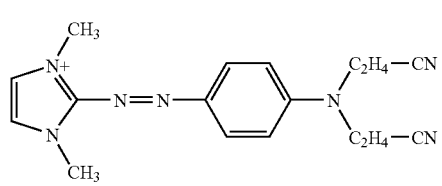 (I13) Cl⁻,
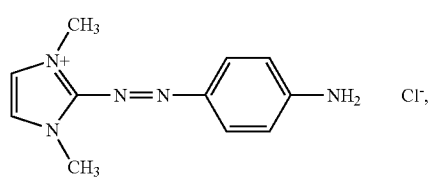 (I14) Cl⁻,
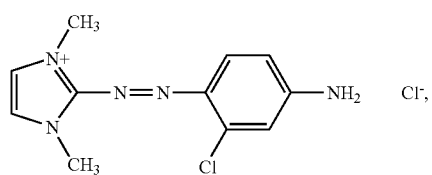 (I15) Cl⁻,
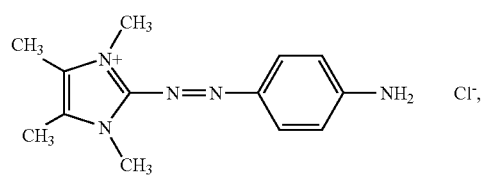 (I16) Cl⁻,
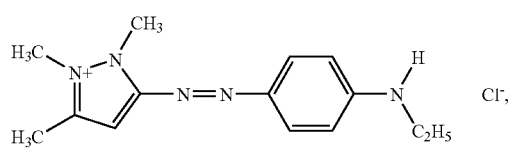 (I17) Cl⁻,
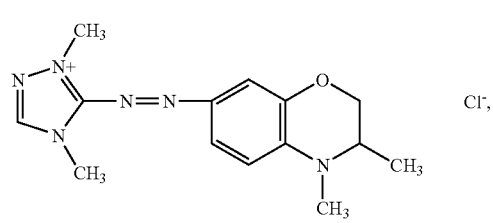 (I18) Cl⁻,
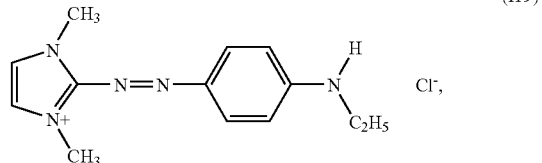 (I19) Cl⁻,
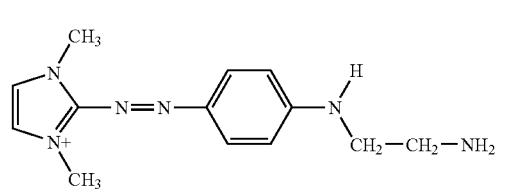 (I20) Cl⁻,
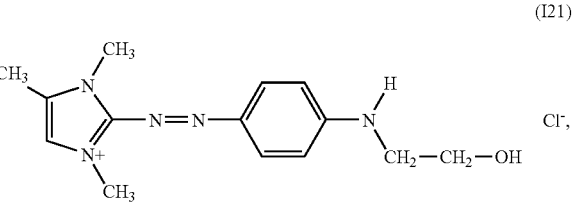 (I21) Cl⁻,
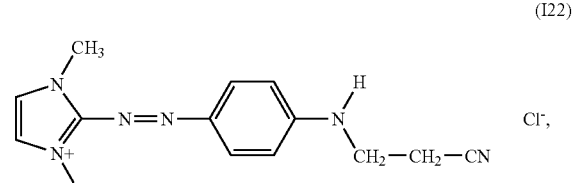 (I22) Cl⁻,
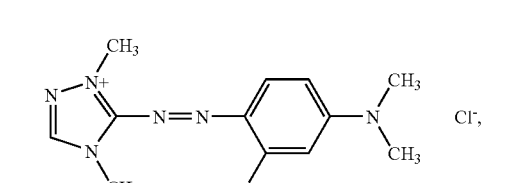 (I23) Cl⁻,
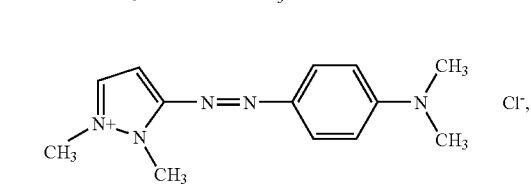 (I24) Cl⁻,

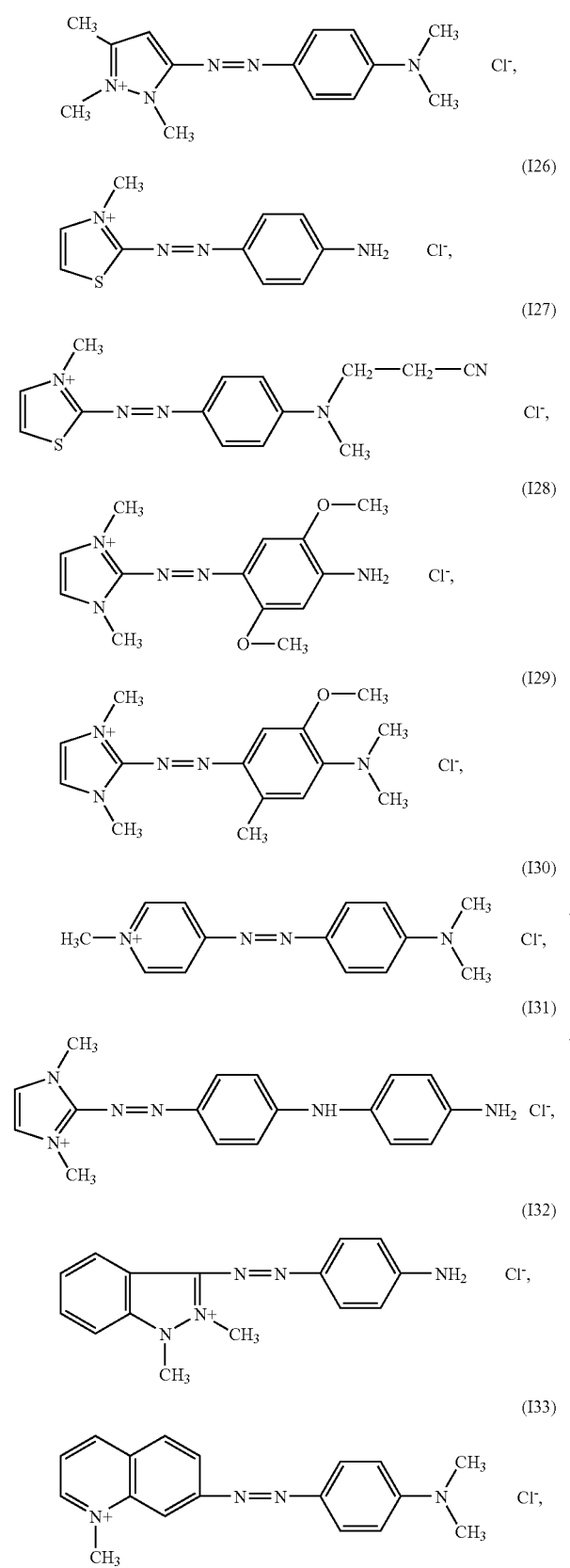
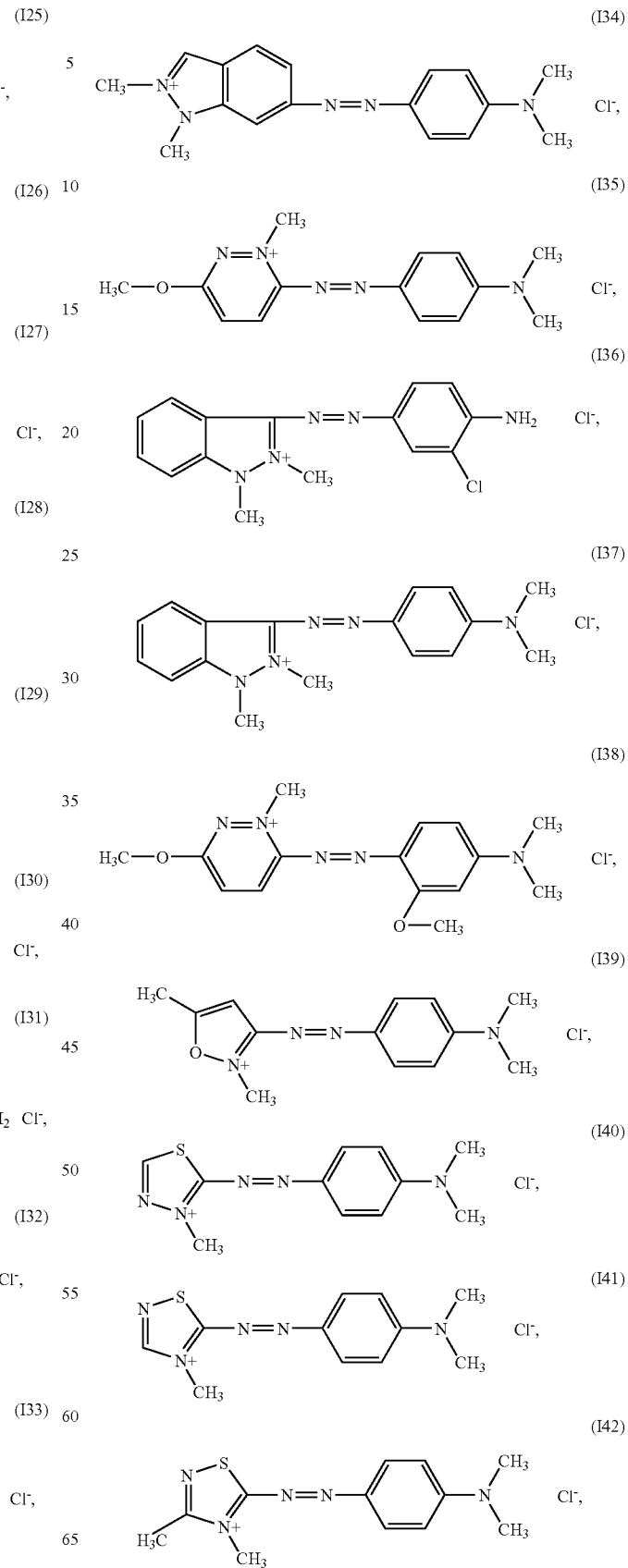

Among the compounds having the structures (I1) to (I54) which are described above, the compounds corresponding to the structures (I1), (I2), (I14) and (I31) are most particularly preferred.

Among the cationic direct dyes of formula (II) which can be used in the dyeing compositions in accordance with the invention, there may be mentioned more particularly the compounds corresponding to the following structures (II1) to (II9):

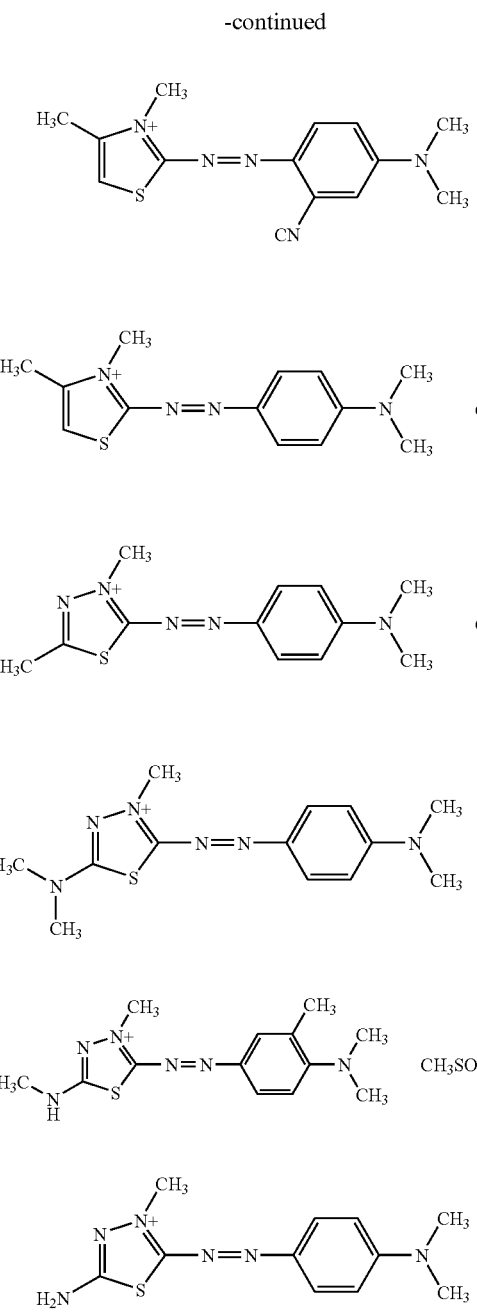
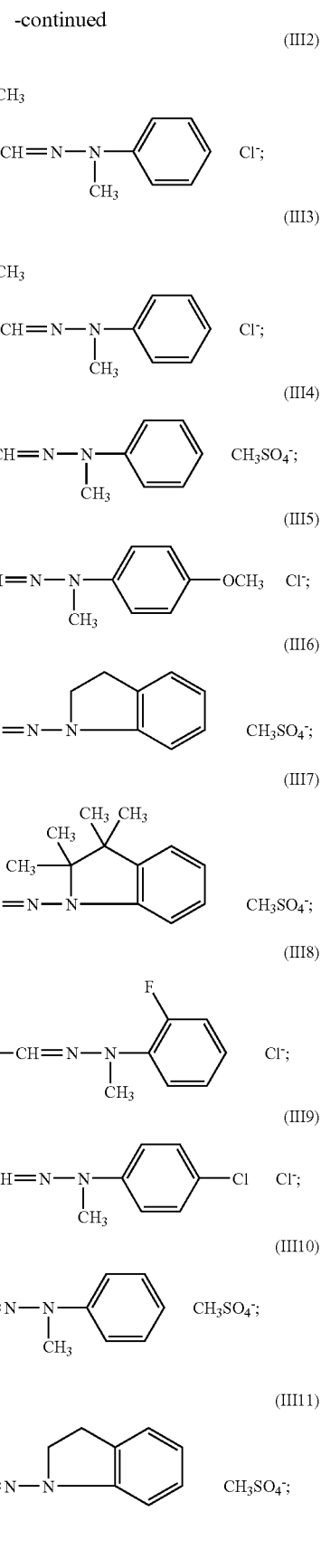
Among the cationic direct dyes of formula (III) which can be used in the dyeing compositions in accordance with the invention, there may be mentioned more particularly the compounds corresponding to the following structures (III1) to (III18):
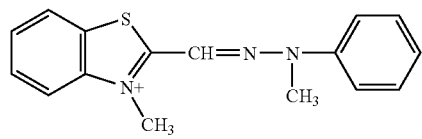

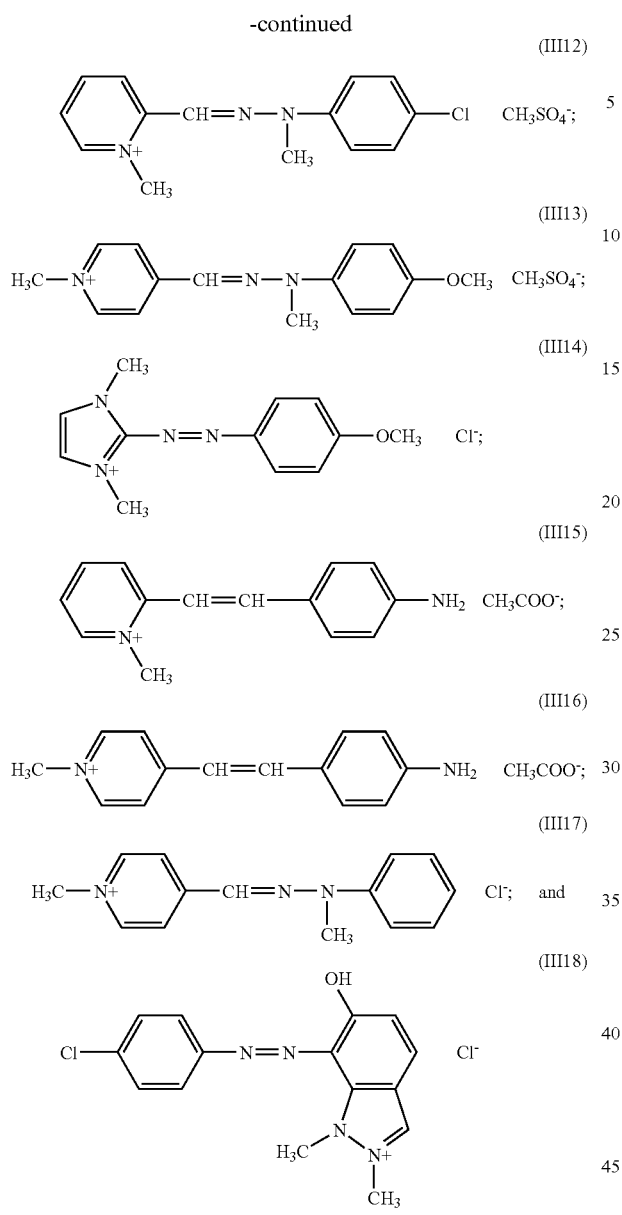

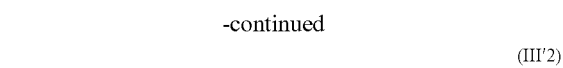

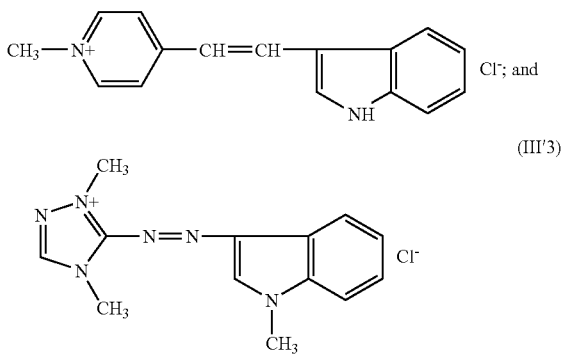

Among the particular compounds having the structures (III1) to (III18) which are described above, the compounds corresponding to the structures (III4), (III5) and (III13) are most particularly preferred.

Among the cationic direct dyes of formula (III') which can be used in the dyeing compositions in accordance with the invention, there may be mentioned more particularly the compounds corresponding to the following structures (III'1) to (III'3):

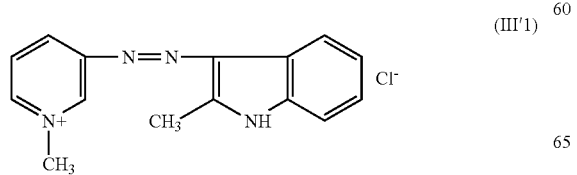

Among the cationic direct dyes of formula (IV) which can be used in the dyeing compositions in accordance with the invention, there may be mentioned more particularly the compounds having the following structures $(IV)_1$ to $(IV)_{77}$:

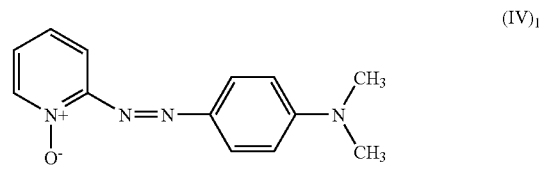

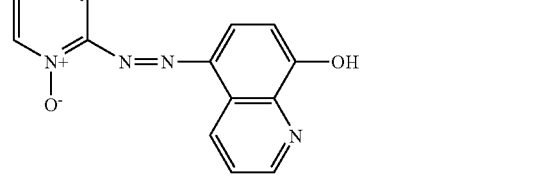

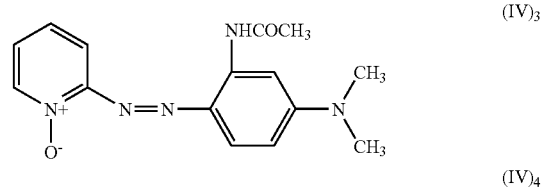

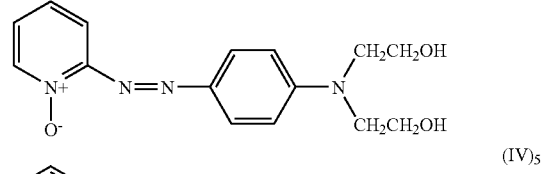

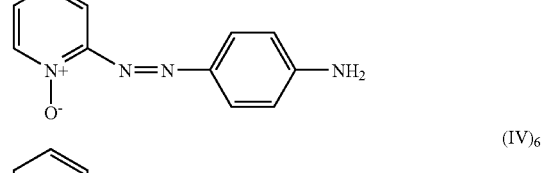

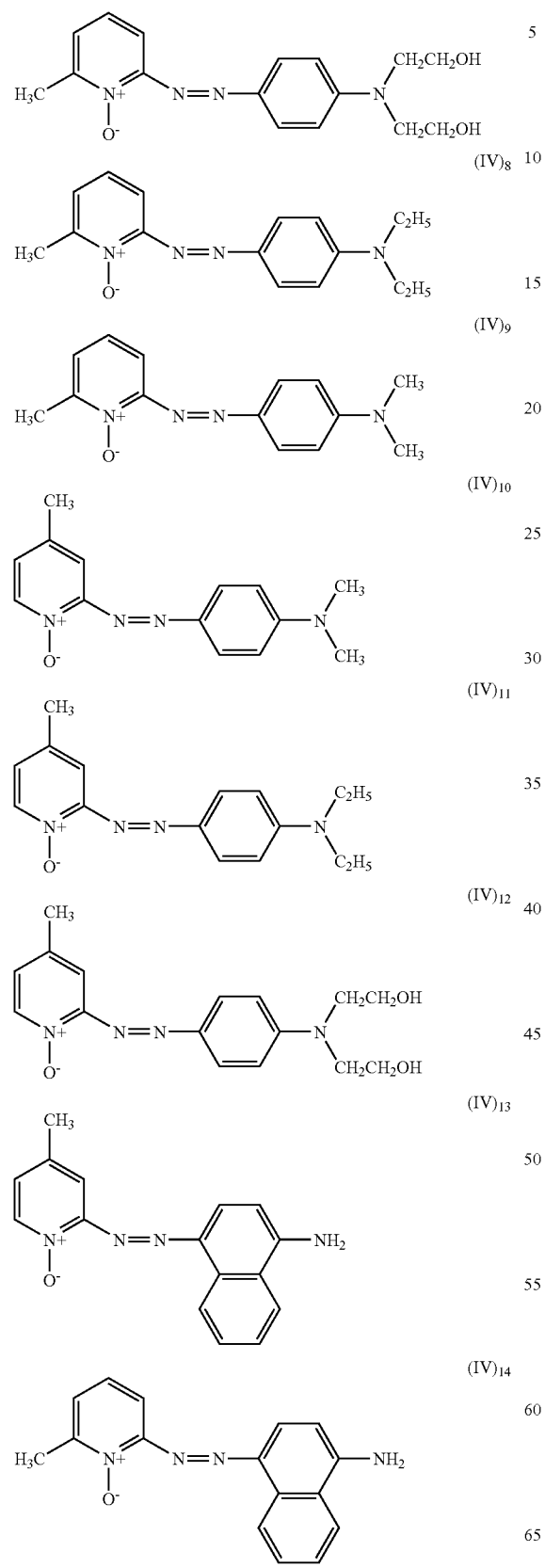

-continued
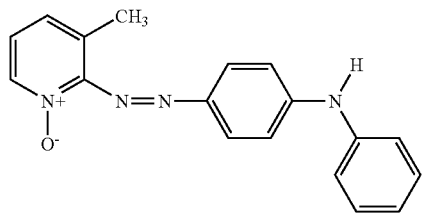 (IV)₂₄
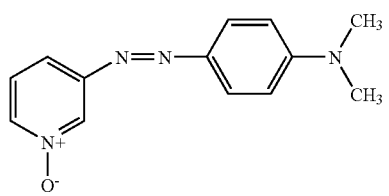 (IV)₂₅
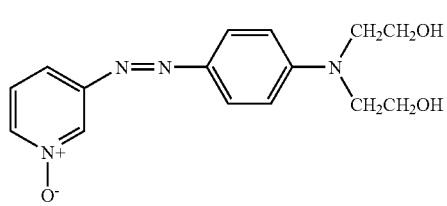 (IV)₂₆
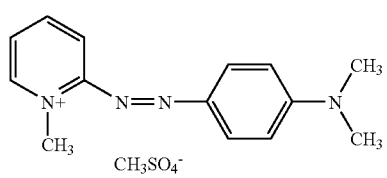 (IV)₂₇
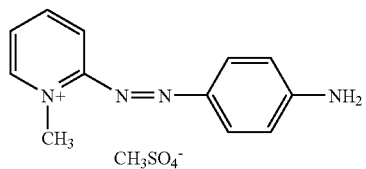 (IV)₂₈
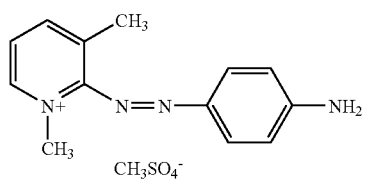 (IV)₂₉
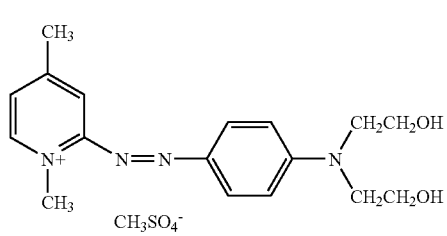 (IV)₃₀
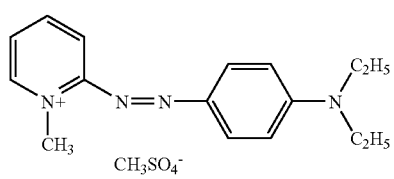 (IV)₃₁
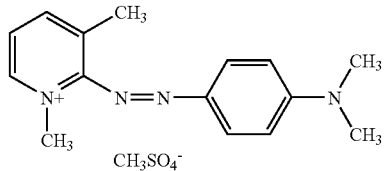 (IV)₃₂
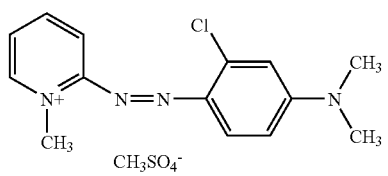 (IV)₃₃
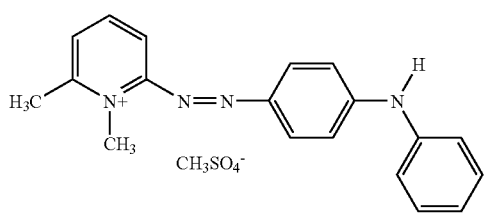 (IV)₃₄
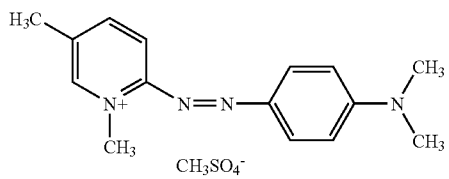 (IV)₃₅
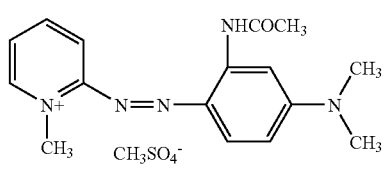 (IV)₃₆
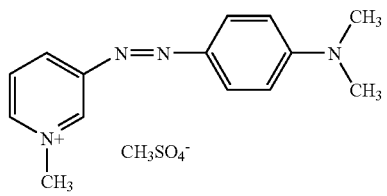 (IV)₃₇
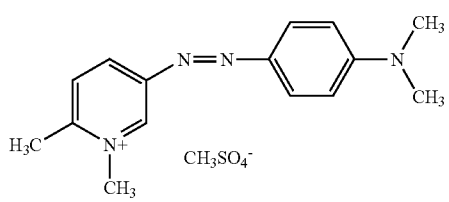 (IV)₃₈
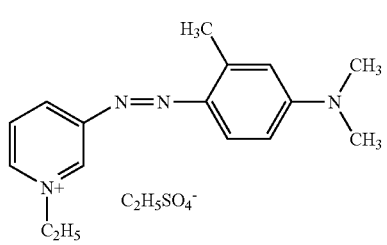 (IV)₃₉

-continued
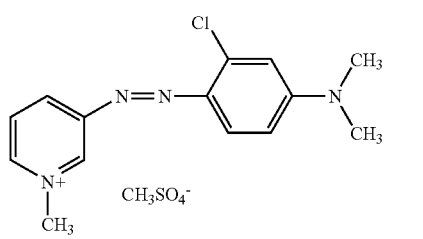 (IV)40
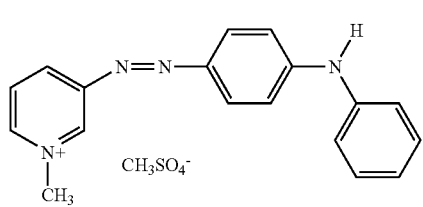 (IV)41
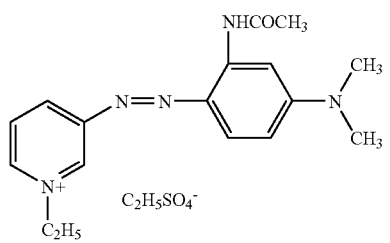 (IV)42
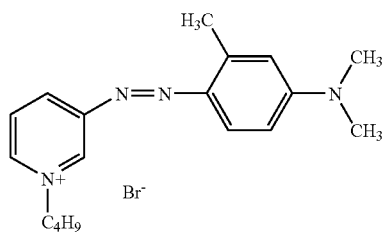 (IV)43
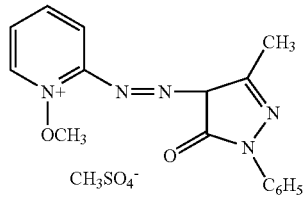 (IV)44
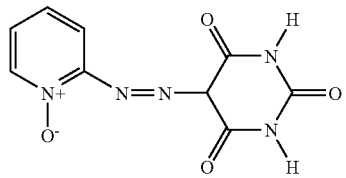 (IV)45
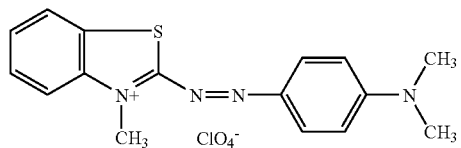 (IV)46
-continued
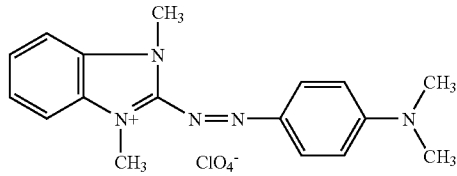 (IV)47
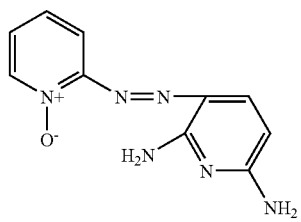 (IV)48
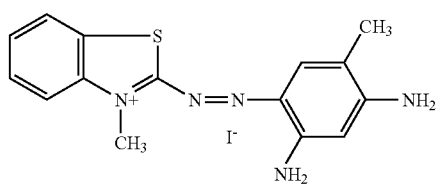 (IV)49
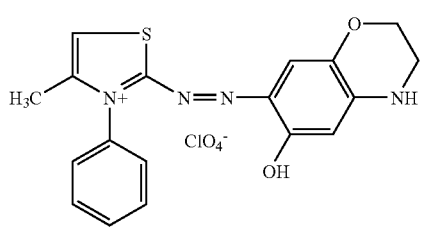 (IV)50
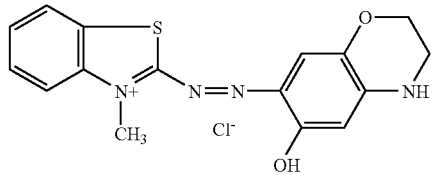 (IV)51
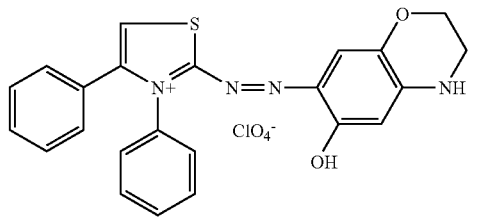 (IV)52
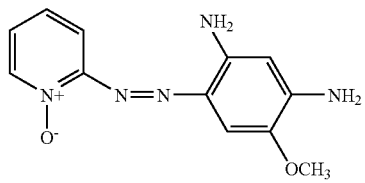 (IV)53
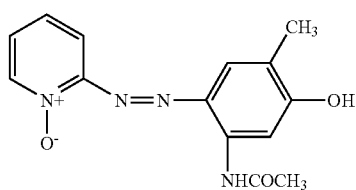 (IV)54

-continued
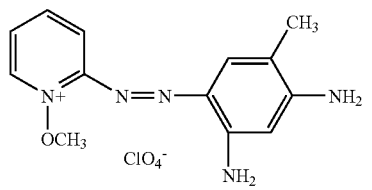 (IV)55
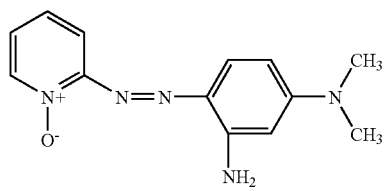 (IV)56
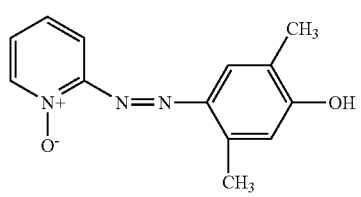 (IV)57
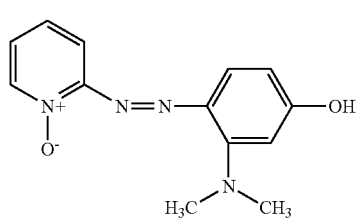 (IV)58
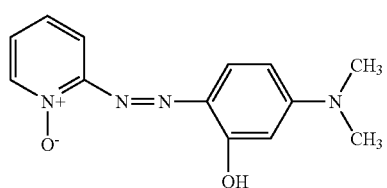 (IV)59
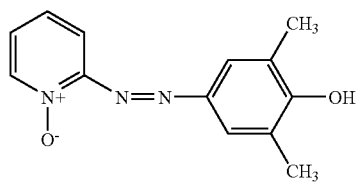 (IV)60
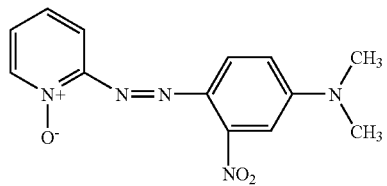 (IV)61
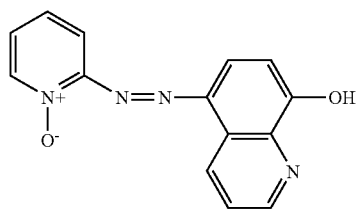 (IV)62
-continued
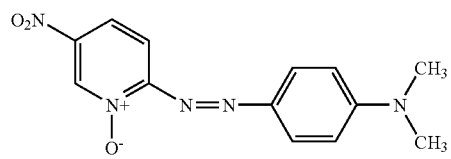 (IV)63
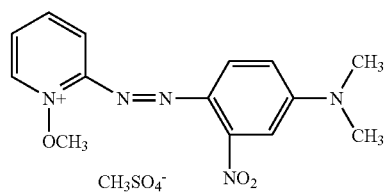 (IV)64
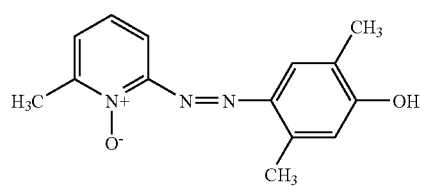 (IV)65
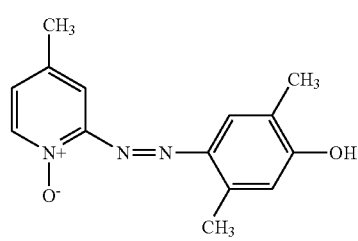 (IV)66
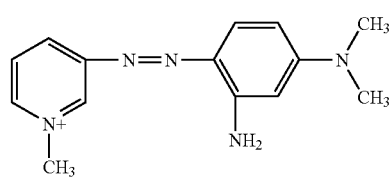 (IV)67
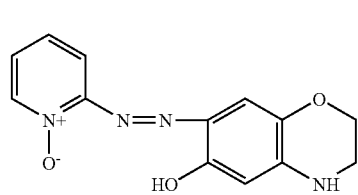 (IV)68
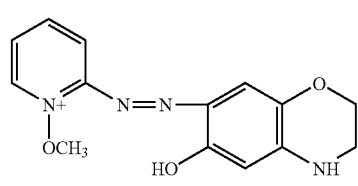 (IV)69
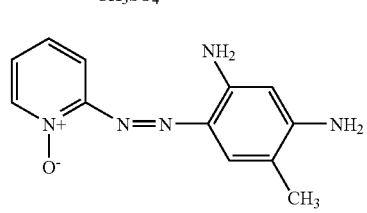 (IV)70

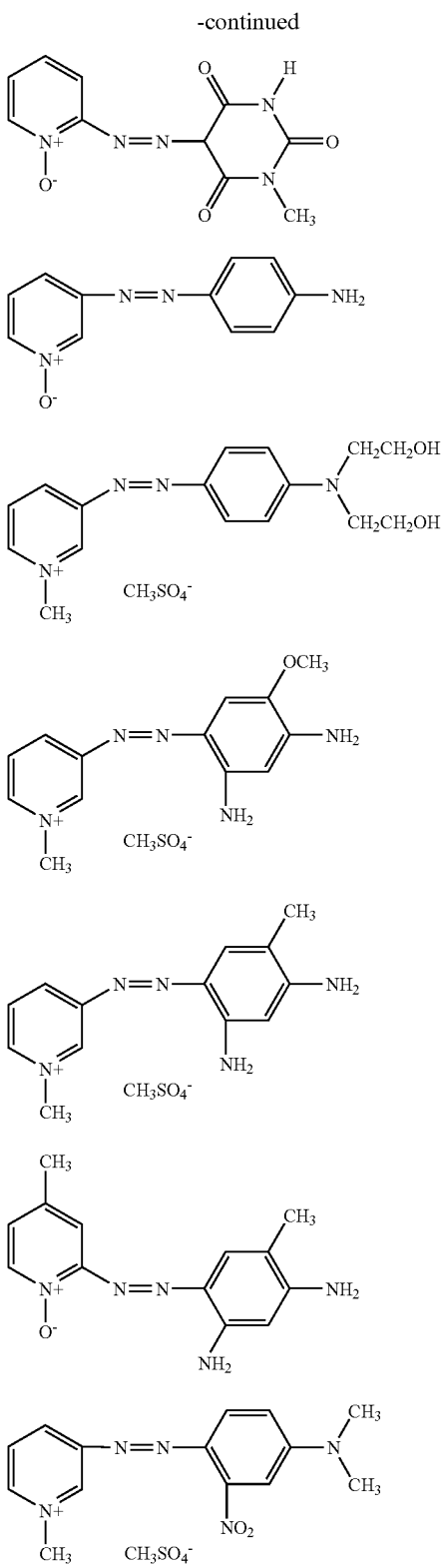

The cationic direct dye(s) used according to the invention preferably represent from 0.001 to 10% by weight approximately of the total weight of the dyeing composition and still more preferably from 0.005 to 5% by weight approximately of this weight.

(ii) The silicones which can be used according to the present invention are chosen from the group consisting of:

$(ii)_1$ aminated silicones, $(ii)_2$ polyoxyalkylenated silicones, $(ii)_3$ silicone gums and resins.

In the whole of the present invention, silicone is understood to mean, in accordance with what is generally accepted, all organosilicon-containing polymers or oligomers having a linear or cyclic, branched or crosslinked, structure of variable molecular weight, which are obtained by polymerization and/or polycondensation of suitably functionalized silanes, and which mainly consist of a repeat of principle motifs in which the silicon atoms are linked to each other by oxygen atoms (siloxane bond ≡Si—O—Si≡), optionally substituted hydrocarbon radicals being directly linked via a carbon atom to the said silicon atoms. The most common hydrocarbon radicals are the alkyl radicals, in particular as $C_1$-$C_{10}$, and in particular methyl, the fluoroalkyl radicals, the aryl, and in particular phenyl, radicals.

According to the invention, aminated silicone denotes any silicone comprising at least one primary, secondary or tertiary amine or a quaternary ammonium group.

Also according to the invention, polyoxyalkylenated silicone denotes any silicone comprising at least one oxyalkylenated group of the $(—C_xH_{2x}O—)_a$ type in which x may vary from 2 to 6, and a is greater than or equal to 2.

In accordance with the invention, the aminated silicones $(ii)_1$ are chosen from:

$(ii)_1(a)$ the compounds which are called in the CTFA dictionary "amodimethicone" and which correspond to the following formula (V):

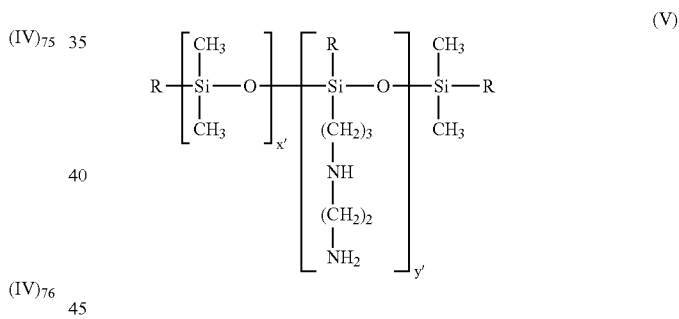

in which R denotes the $CH_3$ or OH radical, and x' and y' are integers which depend on the molecular weight, generally such that the said number-average molecular weight is between 5000 and 500,000 approximately;

$(ii)_1(b)$ the compounds corresponding to the following formula (VI):

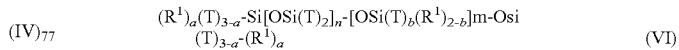

in which,

T is a hydrogen atom, or a phenyl, or OH, or $C_1$-$C_8$ alkyl, and preferably methyl, radical, a denotes the number 0 or an integer from 1 to 3, and preferably 0, b denotes 0 or 1, and in particular 1, m and n are numbers such that the sum (n+m) may vary in particular from 1 to 2000 and in particular from 50 to 150, it being possible for n to denote a number from 0 to 1999 and in particular from 49 to 149 and it being possible for m to denote a number from 1 to 2000, and in particular from 1 to 10;

$R^1$ is a monovalent radical of formula $-C_qH_{2q}L$ in which q is a number from 2 to 8 and L is an optionally quaternized amino group chosen from the groups:

$-N(R^2)-CH_2-CH_2-N(R^2)_2$ $-N(R^2)_2$ $-N^{\oplus}(R^2)_3Q^-$ $-N^{\oplus}(R^2)(H)_2Q^-$ $-N^{\oplus}(R^2)_2HQ^-$ $-N(R^2)-CH_2-CH_2-N^{\oplus}(R^2)(H)_2Q^-$, in which $R^2$ may denote hydrogen, phenyl, benzyl, or a monovalent saturated hydrocarbon radical, for example an alkyl radical having from 1 to 20 carbon atoms and $Q^-$ represents a halide ion such as, for example, fluoride, chloride, bromide or iodide.

A product corresponding to this definition is the polymer which is called in the CTFA dictionary "trimethylsilylamodimethicone", which corresponds to the following formula (VII):

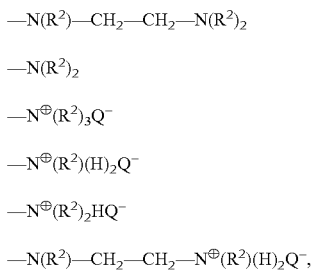

in which n and m have the meanings given above [cf formula (VI)]. Such compounds are described, for example, in patent application EP-A-95238; a compound of formula (VII) is for example sold under the name Q2-8220 by the company OSI.

$(ii)_1(c)$ the compounds which correspond to the following formula (VIII):

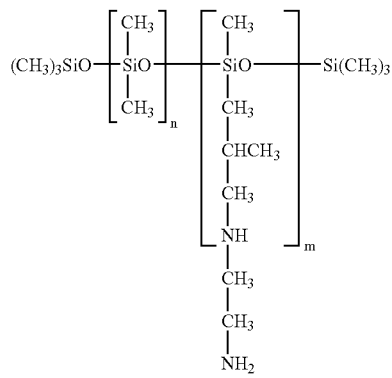

in which, $R^3$ represents a monovalent hydrocarbon radical having from 1 to 18 carbon atoms, and in particular a $C_1$-$C_{18}$ alkyl or $C_2$-$C_{18}$ alkenyl, for example methyl, radical;

$R^4$ represents a divalent hydrocarbon radical, in particular a $C_1$-$C_{18}$ alkylene radical or a $C_1$-$C_{18}$, for example $C_1$-$C_8$, divalent alkyleneoxy radical;

$Q^-$ is a halide, in particular chloride, ion;

r represents a mean statistical value from 2 to 20 and in particular from 2 to 8;

s represents a mean statistical value from 20 to 200 and in particular from 20 to 50.

Such compounds are described more particularly in U.S. Pat. No. 4,185,087.

One compound falling into this class is that sold by the company Union Carbide under the name "Ucar Silicone ALE 56".

When these compounds are used, a particularly advantageous embodiment is their use jointly with cationic and/or nonionic surfactants. By way of example, it is possible to use the product sold under the name "Emulsion Cationique DC 929" by the company Dow Corning, which comprises, in addition to amodimethicone, a cationic surfactant comprising a mixture of products corresponding to the formula:

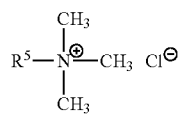

in which $R^5$ denotes alkenyl and/or alkyl radicals having from 14 to 22 carbon atoms derived from tallow fatty acids, and known by the CTFA name "tallowtrimonium chloride", in combination with a nonionic surfactant of formula: $C_9H_{19}-C_6H_4-(OC_2H_4)_{10}-OH$, known by the CTFA name "Nonoxynol 10".

It is also possible to use, for example, the product sold under the name "Emulsio. Catlonique DC 939" by the company Dow Corning, which comprises, in addition to amodimethicone, a cationic surfactant which is trimethylcetylammonium chloride and a nonionic surfactant of formula:

$C_{13}H_{27}-(OC_2H_4)_{12}-OH$, known by the CTFA name "trideceth-12".

Another commercially available product which can be used according to the invention is the product sold under the name "Dow Corning Q2 7224" by the company Dow Corning, comprising, in combination the trimethylsilylamodimethicone of formula (VII) described above, a nonionic surfactant of formula: $C_8H_{17}-C_6H_4-(OCH_2CH_2)_{40}-OH$, known by the CTFA name "octoxynol-40", a second nonionic surfactant of formula: $C_{12}H_{25}-(OCH_2-CH_2)_6-OH$, known by the CTFA name "isolaureth-6", and propylene glycol.

The polyoxyalkylenated silicones $(ii)_2$, according to the present invention are chosen from the compounds having the following general formulae (IX), (X), (XI) and (XII):

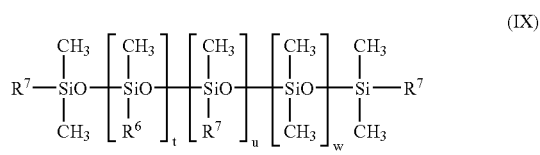

-continued

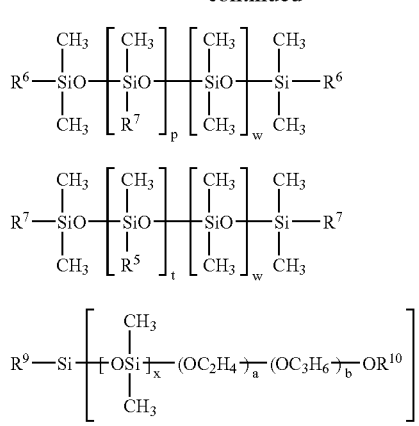

in which formulae (IX), (X), (XI) and (XII), $R^6$, identical or different, represents a $C_1$-$C_{30}$, linear or branched, alkyl radical or a phenyl radical, $R^7$, identical or different, represents a radical —$C_cH_{2c}$—O—$(C_2H_4O)_a(C_3H_6O)_b$—$R^8$ or a radical —$C_cH_{2c}$—O—$(C_4H_8O)_a$—$R^8$, $R^9$, $R^{10}$, which are identical or different, denote a $C_2$-$C_{12}$, linear or branched, alkyl radical, and preferably the methyl radical, $R^8$, identical or different, is chosen from a hydrogen atom, a $C_1$-$C_{12}$, linear or branched, alkyl radical, a $C_1$-$C_6$, linear or branched, alkoxy radical, a $C_2$-$C_{30}$, linear or branched, acyl radical, a hydroxyl radical, an —$SO_3M$ radical, a $C_1$-$C_6$ aminoalkoxy radical which is optionally substituted on the amine, a $C_2$-$C_6$ aminoacyl radical which is optionally substituted on the amine, a radical —$NHCH_2CH_2COOM$, a radical —$N(CH_2CH_2COOM)_2$, an aminoalkyl radical which is optionally substituted on the amine and on the alkyl chain, a $C_2$-$C_{30}$ carboxyacyl radical, a phosphono group which is optionally substituted with one or two substituted aminoalkyl radicals, a radical —$CO(CH_2)_dCOOM$, —$CO$-$CHR^{11}(CH_2)_dCOOM$, —$NHCO(CH_2)_dOH$, —$NH_3Y$, a phosphate group, M, identical or different, denotes a hydrogen atom, Na, K, $L_1$, $NH_4$ or an organic amine, $R^{11}$ denotes a hydrogen atom or an —$SO_3M$ radical, d varies from 1 to 10,
u varies from 0 to 20,
w varies from 0 to 500,
t varies from 0 to 20,
p varies from 1 to 50,
a varies from 0 to 50,
b varies from 0 to 50,
the sum (a+b) is greater than or equal to 2,
c varies from 0 to 4,
x varies from 1 to 100, Y represents a monovalent inorganic or organic anion such as halide (chloride, bromide), sulphate, carboxylate (acetate, lactate, citrate).

These silicones are in particular described in U.S. Pat. Nos. 5,070,171, 5,149,765, 5,093,452 and 5,091,493.

Such silicones are for example marketed by the company RHODIA CHIMIE under the name MIRASIL DMCO, by the company GOLDSCHMIDT under the names ABIL WE 09, ABIL EM 90, ABIL B8852, ABIL B8851, ABIL B 8843, ABIL B8842, by the company DOW CORNING under the names FLUID DC 190, DC 3225 C, Q2-5220, Q25354, Q2-5200, by the company RHONE POULENC under the names SILBIONE HUILE 70646, RHODORSIL HUILE 10634, by the company GENERAL ELECTRIC under the names SF1066, SF1188, by the company SWS SILICONES under the name SILICONE COPOLYMER F 754, by the company AMERCHOL under the name SILSOFT BEAUTY AID SL, by the company SHIN-ETSU under the name KF 351, by the company WACKER under the name BELSIL DMC 6038, by the company SILTECH under the names SILWAX WD-C, SILWAX WD-B, SILWAX WD-IS, SILWAX WSL, SILWAX DCA 100, SILTECH AMINE 65, by the company FANNING CORPORATION under the names FANCORSIL SLA, FANCORSIL LIM1, by the company PHOENIX under the name PECOSIL.

Preferably, according to the present invention, the polyoxyalkylenated silicones corresponding to the general formulae (X) or (XI) are used. More particularly, these formulae correspond to at least one of the, and preferably all of the, following conditions:

c is equal to 2 or 3;
$R^6$ denotes the methyl radical;
$R^8$ represents a methyl radical, a $C_{12}$-$C_{22}$ acyl radical or a —$CO(CH_2)_dCOOM$ radical;
a varies from 2 to 25 and more particularly from 2 to 15,
b is equal to 0,
w varies from 0 to 100,
p varies from 1 to 20.

The polyoxyalkylenated silicones according to the invention may also be chosen from the compounds having the following formula (XIII):

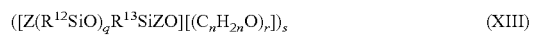

in which, $R^{12}$ and $R^{13}$, which are identical or different, represent a monovalent hydrocarbon radical, n is an integer ranging from 2 to 4, q is a number which is greater than or equal to 4, preferably between 4 and 200 and still more particularly between 4 and 100, r is a number which is greater than or equal to 4, preferably between 4 and 200 and still more particularly between 5 and 100, s is a number which is greater than or equal to 4, preferably between 4 and 1000 and still more particularly between 5 and 300, z represents a divalent organic group which is linked to the adjacent silicon atom by a carbon-silicon bond and to a polyoxyalkylene block by an oxygen atom, the average molecular weight of each siloxane block is between about 400 and about 10,000, that of each polyoxyalkylene block being between about 300 and about 10,000, the siloxane blocks represent from about 10% to about 95% by weight of the block copolymer, it being possible for the number-average molecular weight of the block copolymer to range from 2500 to 1,000,000, and preferably between 3000 and 200,000, and still more particularly between 6000 and 100,000.

$R^{12}$ and $R^{13}$ are preferably chosen from the group comprising linear or branched alkyl radicals such as for example the methyl, ethyl, propyl, butyl, pentyl, hexyl, octyl, decyl or dodecyl radicals, aryl radicals such as for example phenyl or naphthyl, aralkyl or alkylaryl radicals such as for example benzyl or phenylethyl, and tolyl or xylyl radicals.

Z is preferably —R″—, —R″—CO—, —R″—NHCO—, —R″—NH—CO—NH—R‴—, —R″—OCONH—R‴—NHCO—, where R″ is a $C_1$-$C_6$, linear or branched, divalent alkylene group such as for example ethylene, propylene or butylene, and R‴ is a divalent alkylene group or a divalent arylene group such as —$C_6H_4$—, $C_6H_4$—$C_6H_4$—, $C_6H_4$—$CH_2$—$C_6H_4$—, —$C_6H_4$—$C(CH_3)_2C_6H_4$—.

Still more preferably, Z represents a divalent alkylene radical, more particularly the —$C_3H_6$— radical or the —$C_4H_8$— radical, which are linear or branched.

The preparation of the block copolymers used in the context of the present invention is described in European application EP-0,492,657 A1, whose teaching is included in the present description.

Such products are for example marketed under the name SILICONE FLUID FZ-2172 by the company OSI.

The silicone gums and resins $(ii)_3$, according to the present invention, are chosen in particular as regards:

$(ii)_3$(a) the gums, from the polydiorganosiloxanes having high molecular masses of between 200,000 and 1,000,000; the following gums may be mentioned:
  poly[(dimethylsiloxane)/(methylvinylsiloxane)],
  poly[(dimethylsiloxane)/(diphenylsiloxane)],
  poly[(dimethylsiloxane)/(phenylmethylsiloxane)],
  poly[(dimethylsiloxane)/(diphenylsiloxane)/(methylvinylsiloxane)].

The silicone resins are crosslinked siloxane systems containing $R_2SiO_{2/2}$, $RSiO_{3/2}$ and $SiO_{4/2}$ units in which R represents a hydrocarbon group possessing 1 to 6 carbon atoms or a phenyl group. Among these products, those which are particularly preferred are those in which R denotes a lower alkyl radical or a phenyl radical.

There may be mentioned in particular among these resins, the product sold by the company DOW CORNING under the name DOW CORNING 593, which is a mixture of trimethylsiloxysilicate and of polydimethylsiloxane, or the products sold by the company GENERAL ELECTRIC under the names SILICONE FLUID SS 4230 and SS 4267, which are dimethyl/trimethyl/polysiloxanes.

Among all the silicones described above, there are preferably used according to the present invention the aminated silicones identified by the reference $(ii)_1(a)$, that is to say those corresponding to the formula (V) described above, the aminated silicones identified by the reference $(ii)_1(b)$ and having the formula (VII) described above, and the polyoxyalkylenated silicones identified by the reference $(ii)_2$ and having the respective formulae (X) and (XI) described above.

The silicone(s) (ii) used according to the invention preferably represent from 0.01 to 20% by weight approximately of the total weight of the dyeing composition and still more preferably from 0.1 to 10% by weight approximately of this weight.

The appropriate dyeing medium (or carrier) generally consists of water or of a mixture of water and of at least one organic solvent for solubilizing the compounds which would not be sufficiently soluble in water. As organic solvent, there may be mentioned for example the $C_1$-$C_4$ lower alkanols such as ethanol and isopropanol, the aromatic alcohols such as benzyl alcohol as well as similar products and mixtures thereof.

The solvents may be present in proportions preferably of between 1 and 40% by weight approximately relative to the total weight of the dyeing composition, and still more preferably between 5 and 30% by weight approximately.

The pH of the dyeing composition in accordance with the invention is generally between 2 and 11 approximately, and preferably between 5 and 10 approximately. It may be adjusted to the desired value by means of acidifying or alkalinizing agents normally used in dyeing keratinous fibres.

Among the acidifying agents, there may be mentioned, by way of example, the inorganic or organic acids such as hydrochloric acid, orthophosphoric acid, sulphuric acid, carboxylic acids such as acetic acid, tartaric acid, citric acid, lactic acid, sulphonic acids.

Among the alkalinizing agents, there may be mentioned, by way of example, aqueous ammonia, alkali metal carbonates, alkanolamines such as mono-, di- and triethanolamines as well as derivatives thereof, sodium or potassium hydroxides and the compounds having the following formula (XIV):

in which W is a propylene residue which is optionally substituted with a hydroxyl group or a $C_1$-$C_6$ alkyl radical; $R^{14}$, $R^{15}$, $R^{16}$ and $R^{17}$, which are identical or different, represent a hydrogen atom, a $C_1$-$C_6$ alkyl radical or a $C_1$-$C_6$ hydroxyalkyl radical.

The dyeing composition in accordance with the invention may, in addition to the cationic direct dye(s) (i) defined above, contain one or more additional direct dyes which may for example be chosen from the nitrobenzene dyes, the anthraquinone dyes, the naphthoquinone dyes, the triarylmethane dyes, the xanthene dyes, the noncationic azo dyes.

When it is intended for oxidation dyeing, the dyeing composition in accordance with the invention contains, in addition to the cationic direct dye(s) (i), one or more oxidation bases chosen from the oxidation bases conventionally used for oxidation dyeing and among which there may be mentioned in particular the para-phenylenediamines, the bis-phenylalkylenediamines, the para-aminophenols, the ortho-aminophenols and the heterocyclic bases. When they are used, the oxidation base(s) preferably represent from 0.0005 to 12% by weight approximately of the total weight of the dyeing composition, and still more preferably from 0.005 to 6% by weight approximately of this weight.

When it is intended for oxidation dyeing, the dyeing composition in accordance with the invention may also contain, in addition to the cationic direct dye (i) and the silicone (ii) as well as oxidation bases, one or more couplers so as to modify or increase the shimmer of the shades obtained using the cationic direct dye(s) (i) and the oxidation base(s).

The couplers which can be used in the dyeing composition in accordance with the invention may be chosen from the couplers conventionally used in oxidation dyeing and among which there may be mentioned in particular the meta-phenylenediamines, the meta-aminophenols, the meta-diphenols and the heterocyclic couplers.

When they are present, the coupler(s) preferably represent from 0.0001 to 10% by weight approximately of the total weight of the dyeing composition and still more preferably from 0.005 to 5% by weight approximately of this weight.

The dyeing composition in accordance with the invention may also contain various adjuvants which are conventionally used in hair-dyeing compositions, such as antioxidants, penetrating agents, sequestrants, perfumes, buffers, dispersing agents, film-forming agents, ceramides, preservatives, screening agents and opacifying agents.

Of course, persons skilled in the art will be careful to choose this or these optional additional compounds such that the advantageous properties intrinsically attached to the dyeing composition in accordance with the invention are not, or not substantially, altered by the addition(s) envisaged.

The dyeing composition according to the invention may be provided in various forms, such as in the form of liquids, shampoos, creams, gels, or in any other form appropriate for dyeing keratinous fibres, and in particular human hair. It may be obtained by freshly mixing a composition, which is optionally pulverulent, containing the cationic direct dye(s) with a composition containing the silicone.

When the combination of the cationic direct dye (i) and of the silicone (ii) according to the invention is used in a composition intended for oxidation dyeing (one or more oxidation bases are then used, optionally in the presence of one or more couplers) or when it is used in a composition intended for direct lightening dyeing, then the dyeing composition in accordance with the invention contains, in addition, at least one oxidizing agent chosen for example from hydrogen peroxide, urea peroxide, alkali metal bromates, persalts such the perborates and persulphates, and enzymes such as peroxidases, laccases and oxidoreductases containing two electrons. The use of hydrogen peroxide or of enzymes is particularly preferred.

Another subject of the invention is a method of dyeing keratinous fibres and in particular human keratinous fibres such as hair using the dyeing composition as defined above.

According to a first variant of this dyeing method in accordance with the invention, at least one dyeing composition as defined above is applied to the fibres for a sufficient time to develop the desired colour, after which they are rinsed, optionally washed with shampoo, rinsed again and dried.

The time necessary for the development of the colour on the keratinous fibres is generally between 3 and 60 minutes and still more preferably 5 and 40 minutes.

According to a second variant of this dyeing method in accordance with the invention, at least one dyeing composition as defined above is applied to the fibres for a sufficient time to develop the desired colour, with no final rinsing.

According to a particular embodiment of this dyeing method, and when the dyeing composition in accordance with the invention contains at least one oxidation base and at least one oxidizing agent, the dyeing method comprises a preliminary stage consisting of storing in a separate form, on the one hand, a composition (A1) comprising, in an appropriate dyeing medium, at least one cationic direct dye (i) as defined above and at least one oxidation base and, on the other hand, a composition (B1) containing, in an appropriate dyeing medium, at least one oxidizing agent, and then mixing them at the time of use before applying this mixture to the keratinous fibres, the composition (A1) or the composition (B1) containing the silicone (ii) as defined above.

According to another particular embodiment of this dyeing method, and when the dyeing composition in accordance with the invention contains at least one oxidizing agent, the dyeing method comprises a preliminary stage consisting of storing in a separate form, on the one hand, a composition (A2) comprising, in an appropriate dyeing medium, at least one cationic direct dye (i) as defined above and, on the other hand, a composition (B2) containing, in an appropriate dyeing medium, at least one oxidizing agent, and then mixing them at the time of use before applying this mixture to the keratinous fibres, the composition (A2) or the composition (B2) containing the silicone as defined above.

Another subject of the invention is a multicompartment device or dyeing "kit" or any other multicompartment packaging system in which a first compartment contains composition (A1) or (A2) as defined above and a second compartment contains composition (B1) or (B2) as defined above. These devices may be equipped with a means allowing the desired mixture to be delivered to the hair, such as the devices described in patent FR-2,586,913 in the applicant's name.

The following examples are intended to illustrate the invention without, however, limiting the scope thereof.

EXAMPLES

Examples 1 to 2

The two direct dyeing compositions which are assembled in the following table were prepared:

(all contents expressed in grams)

|  | EXAMPLES No. | |
|---|---|---|
|  | 1 | 2 |
| Cationic direct dye of formula (I1) | 0.10 | |
| Cationic direct dye of formula (I14) | 0.10 | |
| Cationic direct dye of formula (IV)$_{27}$ | | 0.10 |
| Nonylphenol containing 9 moles of ethylene oxide | 8.0 | 8.0 |
| Aminated silicone (mixture of polydimethylsiloxane containing aminoethyl-aminoisobutyl/-polydimethylsiloxane groups), sold under the name Q2-8220 by the company OSI | 1.2 | |
| Polyoxyalkylenated silicone (oxyethylenated polydimethylsiloxane containing 22 EO and oxypropylenated polydimethylsiloxane containing 23 PO), sold under the name MIRASIL DMCO by the company RHODIA CHIMIE | | 0.75 |
| Ethanol | 10 | 10 |
| 2-Amino-2-methyl-l-propanol qs | pH 9 | pH 9 |
| Demineralized water qsp | 100 | 100 |

The above compositions were each applied for 30 minutes to locks of natural grey hair which is 90% white. The hair locks were then rinsed, washed with a standard shampoo and then dried.

The locks were dyed in the following shades:

| Examples | Shades obtained |
|---|---|
| 1 | dark orange-red |
| 2 | dark purple |

What is claimed is:

1. A composition for dyeing keratinous fibers comprising (i) at least one cationic direct dye chosen from compounds having the following formulae (I), or (III):
   a) compounds of following formula (I):

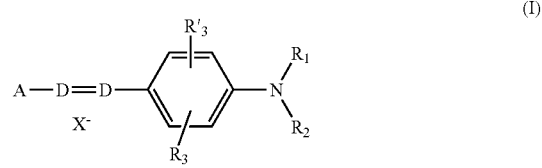

wherein:
- D is a nitrogen atom or a —CH group,
- $R_1$ and $R_2$, which are identical or different, are chosen from a hydrogen atom; a ($C_1$-$C_4$) alkyl radical which may be unsubstituted or substituted with a —CN radical, an —OH radical or an —NH$_2$ radical or form with each other or with a carbon atom of the benzene ring an optionally oxygen-containing or nitrogen-containing heterocycle which may be unsubtituted or substituted with at least one radical chosen from ($C_1$-$C_4$) alkyl radicals; and a 4'-aminophenyl radical,
- $R_3$ and $R'_3$, which are identical or different, are chosen from a hydrogen atom; a halogen atom chosen from chlorine, bromine, iodine, and fluorine; a cyano group; a ($C_1$-$C_4$) alkyl radical; a ($C_1$-$C_4$) alkoxy radical; and a ($C_1$-$C_4$) acetyloxy radical,
- $X^-$ is an anion,
- A is chosen from the following structures $A_1$, $A_7$, and $A_{19}$:

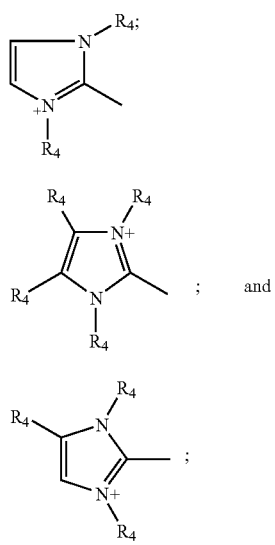

wherein:
- $R_4$ is a ($C_1$-$C_4$) alkyl radical which may be unsubstituted or substituted with a hydroxyl radical, and
- $R_5$ is a ($C_1$-$C_4$) alkoxy radical; and b) compounds of following formulae (III):

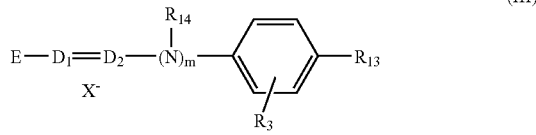

wherein:
- $R_{13}$ is chosen from a hydrogen atom, a ($C_1$-$C_4$) alkoxy radical, a halogen atom chosen from bromine, chlorine, iodine and fluorine atoms, and an amino radical,
- $R_{14}$ is chosen from a hydrogen atom, and a ($C_1$-$C_4$) alkyl radical, or forms, with a carbon atom of the benzene ring, a heterocycle which optionally contains an oxygen heteroatom and which is unsubstituted or substituted with at least one radical chosen from ($C_1$-$C_4$) alkyl radicals,
- $R_{15}$ is a hydrogen atom or a halogen atom chosen from bromine, chlorine, iodine and fluorine,
- $D_1$ and $D_2$, which are identical or different, are a nitrogen atom or a —CH group,
- m is 0 or 1, with the proviso that when $R_{13}$ is an unsubstituted amino group, then $D_1$ and $D_2$ simultaneously are a —CH group and m is 0,

- $X^-$ is an anion,
- E is a group chosen from the following structures E1, E2, and E7:

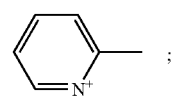

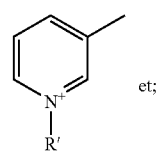

wherein R' is a ($C_1$-$C_4$) alkyl radical;

wherein said composition further comprises (ii) at least one silicone chosen from:
- (ii)$_1$—aminated silicones
- (ii)$_2$—polyoxyalkylenated silicones; and
- (ii)$_3$—silicone gums and resins.

2. A composition according to claim 1, wherein the keratinous fibers are human keratinous fibers.

3. A composition according to claim 2, wherein the human keratinous fibers are hair.

4. A composition according to claim 1, wherein the composition further comprises a medium suitable for dyeing.

5. A composition according to claim 1, wherein in formula (I) and (III), $X^-$ is chosen from chloride, methylsulphate, and acetate.

6. A composition according to claim 1, wherein the compounds of formula (I) are chosen from compounds having following structures:

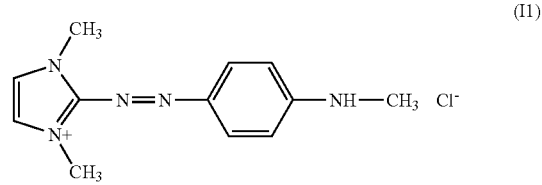

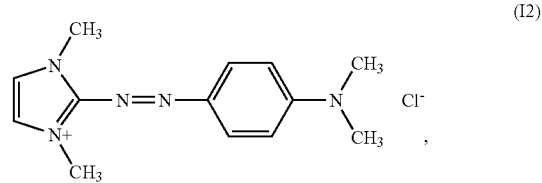

-continued
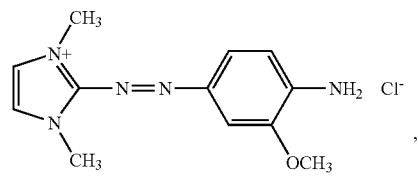 (I11)
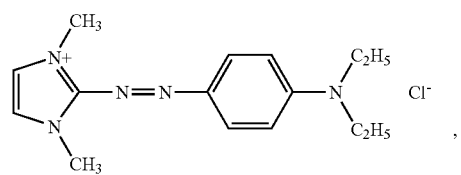 (I12)
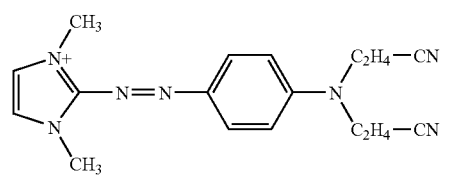 (I13)
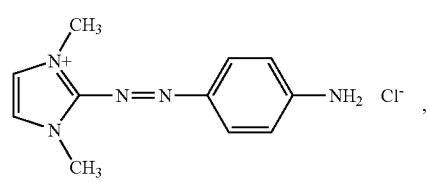 (I14)
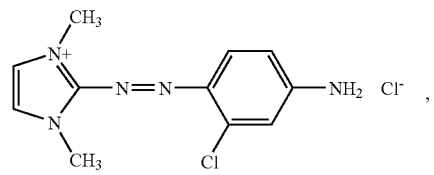 (I15)
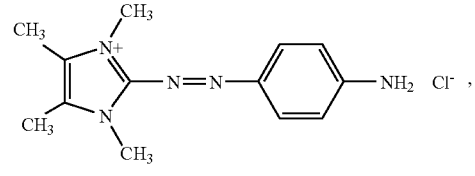 (I16)
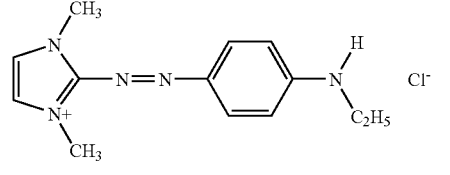 (I19)
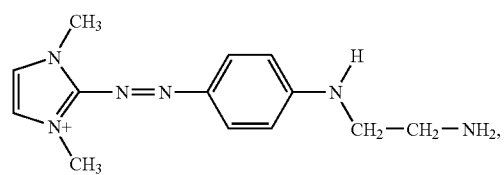 (I20)
-continued
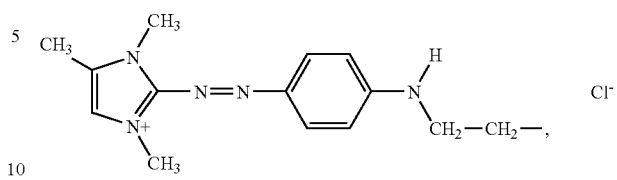 (I21)
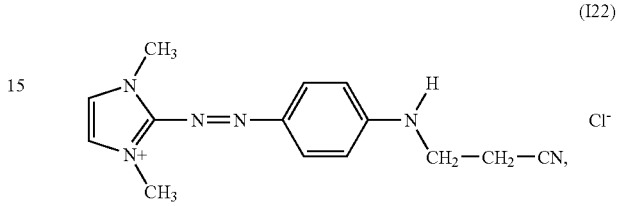 (I22)
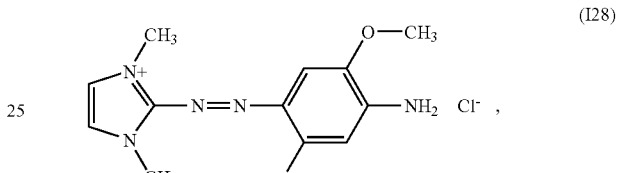 (I28)
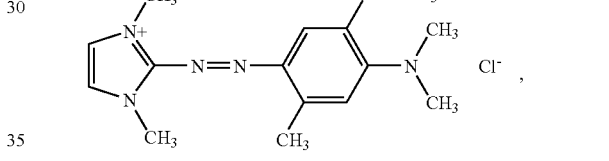 (I29)
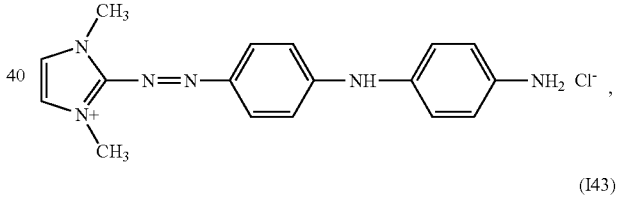 (I31)
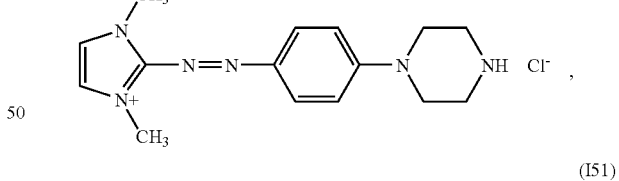 (I43)
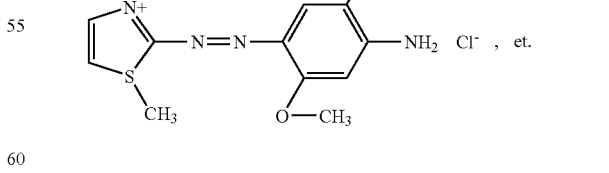 (I51)
, et.
7. A composition according to claim 6, wherein the cationic direct dyes are chosen from the structures (I1), (I2), (I14), and (I31).
8. A composition according to claim 1, wherein the compounds of formula (III) are chosen from compounds having the following structures:

(III4) H₃C—N⁺(pyridinium)—CH=N—N(CH₃)—phenyl   CH₃SO₄⁻ ;

(III5) H₃C—N⁺(pyridinium)—CH=N—N(CH₃)—phenyl—OCH₃   Cl⁻ ;

(III6) H₃C—N⁺(pyridinium)—CH=N—N(indoline)   CH₃SO₄⁻ ;

(III7) H₃C—N⁺(pyridinium)—CH=N—N(2,2,3,3-tetramethylindoline)   CH₃SO₄⁻ ;

(III8) H₃C—N⁺(pyridinium)—CH=N—N(CH₃)—(2-fluorophenyl)   Cl⁻ ;

(III9) H₃C—N⁺(pyridinium)—CH=N—N(CH₃)—phenyl—Cl   Cl⁻ ;

(III10) (2-pyridinium, N-CH₃)—CH=N—N(CH₃)—phenyl   CH₃SO₄⁻ ;

(III11) (2-pyridinium, N-CH₃)—CH=N—N(indoline)   CH₃SO₄⁻ ;

(III12) (2-pyridinium, N-CH₃)—CH=N—N(CH₃)—phenyl—Cl   CH₃SO₄⁻ ;

(III13) H₃C—N⁺(pyridinium)—CH=N—N(CH₃)—phenyl—OCH₃   CH₃SO₄⁻ ;

-continued (III15) (2-pyridinium, N-CH₃)—CH=CH—phenyl—NH₂   CH₃COO⁻ ;

(III16) H₃C—N⁺(pyridinium)—CH=CH—phenyl—NH₂   CH₃COO⁻ ;

(III17) H₃C—N⁺(pyridinium)—CH=N—N(CH₃)—phenyl   Cl⁻ ; et.

9. A composition according to claim 8, wherein the cationic direct dyes of formula (III) are chosen from the compounds having to the structures (III4), (III5) and (III13).

10. A composition according to claim 1, wherein said at least one cationic direct dye is present in an amount ranging from 0.001 to 10% by weight of the total weight of the composition.

11. A composition according to claim 10, wherein said at least one cationic direct dye is present in an amount ranging from 0.005 to 5% by weight of the total weight of the composition.

12. A composition according to claim 1, wherein said aminated silicone (ii)₁ is a compound of the following formula (V):

$$R-\underset{CH_3}{\underset{|}{\overset{CH_3}{\overset{|}{Si}}}}-O-\left[\underset{CH_3}{\underset{|}{\overset{CH_3}{\overset{|}{Si}}}}-O\right]_{x'}-\left[\underset{(CH_2)_3}{\underset{|}{\overset{R}{\overset{|}{Si}}}}-O\right]_{y'}-\underset{CH_3}{\underset{|}{\overset{CH_3}{\overset{|}{Si}}}}-R$$

with side chain $(CH_2)_3-NH-(CH_2)_2-NH_2$ wherein:
R is a CH₃ group or an OH radical, and
x' and y' are integers which depend on the molecular weight.

13. A composition according to claim 1, wherein the aminated silicone (ii)₁ is chosen from compounds having the following formula (VI):

$$(R^1)_a(T)_{3-a}\text{-Si}(OSi(T)_2)_n\text{-}(OSi(T)_b(R^1)_{2-b})_m\text{—OSi}(T)_{3-a}\text{-}(R^1)_a \quad (VI)$$

wherein:
T is chosen from a hydrogen atom, a phenyl, an OH radical, and a (C₁-C₈) alkyl radical,
a is the number 0 or an integer ranging from 1 to 3,
b is 0 or 1,
m and n are integers such that the sum (n+m) varies from 1 to 2000, n is an integer ranging from 0 to 1999 and m is an integer ranging from 1 to 2000;

$R^1$ is a monovalent radical of formula —$C_qH_{2q}L$ wherein q is an integer ranging from 2 to 8 and L is an optionally quaternized amino group chosen from the groups:
—N($R^2$)—CH$_2$—CH$_2$—N($R^2$)$_2$; —N—($R^2$)$_2$; —N—($R^2$)$_3$Q$^-$; —N—($R^2$)(H)$_2$Q$^-$; —N—($R^2$)$_2$HQ$^-$; —N($R^2$)—CH$_2$—CH$_2$—N$^\square$($R^2$)(H)$_2$Q$^-$, wherein $R_2$ is chosen from a hydrogen, phenyl, benzyl, and a monovalent saturated hydrocarbon radical, and Q$^-$ represents a halide ion.

14. A composition according to claim 13, wherein T is a methyl radical.

15. A composition according to claim 13, wherein a is zero.

16. A composition according to claim 14, wherein b is 1.

17. A composition according to claim 13, wherein m and n are integers such that the sum (n+m) varies from 50 to 150.

18. A composition according to claim 13, wherein n is an integer ranging from 1 to 10.

19. A composition according to claim 13, wherein m is an integer ranging from 49 to 149.

20. A composition according to claim 13, wherein $R^2$ is an alkyl radical having from 1 to 20 carbon atoms.

21. A composition according to claim 13, wherein the aminated silicone is chosen from compounds having the following formula (VII):

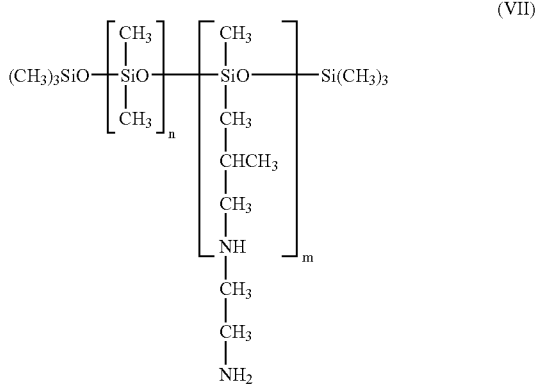

wherein n and m have the meanings given for the formula (VI).

22. A composition according to claim 1, wherein the aminated silicone (ii)$_1$ is chosen from compounds having the following formula (VIII):

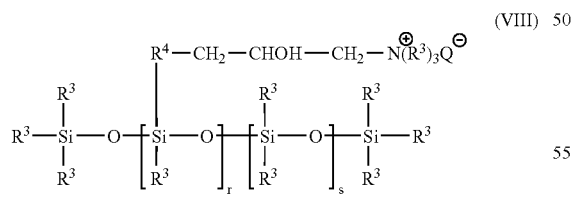

wherein
$R^3$ is a monovalent hydrocarbon radical having from 1 to 18 carbon atoms;
$R^4$ is a divalent hydrocarbon radical;
$Q^{31}$ is a halide ion;
r is a mean statistical value ranging from 2 to 20; and
s is a mean statistical value from 20 to 200.

23. A composition according to claim 22, wherein $R^3$ is chosen from a (C$_1$-C$_{18}$)alkyl and a (C$_2$-C$_{18}$) alkenyl radical.

24. A composition according to claim 22, wherein $R^4$ is chosen from a (C$_1$-C$_{18}$) alkylene radical and a (C$_1$-C$_{18}$) divalent alkyleneoxy radical.

25. A composition according to claim 22, wherein r is a mean statistical value ranging from 2 to 8.

26. A composition according to claim 22, wherein s is a mean statistical value ranging from 20 to 50.

27. A composition according to claim 1, wherein the polyoxyalkylenated silicone (ii)$_2$ is chosen from compounds having the following formulae (IX), (X), (XI) and (XII):

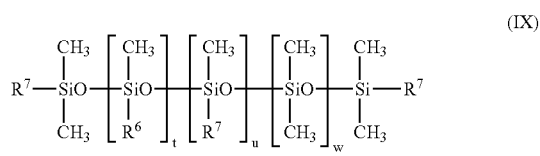

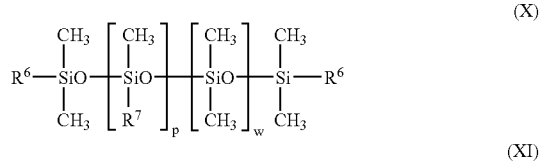

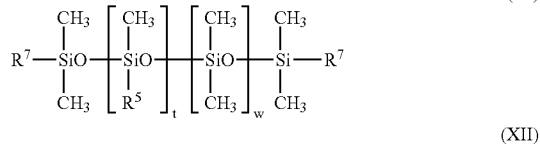

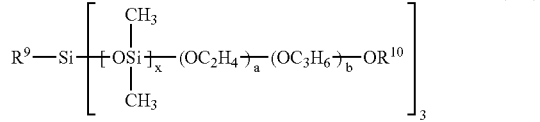

wherein:
$R^6$, identical or different, is chosen from a (C$_1$-C$_{30}$), linear or branched, alkyl radical and a phenyl radical,
$R^7$, identical or different, is chosen from a radical —C$_c$H$_{2c}$—O—(C$_2$H$_4$O)$_a$(C$_3$H$_6$O)$_b$—R$^8$ and a radical —C$_c$H$_{2c}$—O—(C$_4$H$_8$O)$_a$—R$^8$,
$R^9$, $R^{10}$, which are identical or different, are a (C$_2$-C$_{12}$), linear or branched, alkyl radical,
$R^8$, identical or different, is chosen from a hydrogen atom, a (C$_1$-C$_{12}$), linear or branched, alkyl radical, a (C$_1$-C$_6$), linear or branched, alkoxy radical, a (C$_2$-C$_{30}$), linear or branched, acyl radical, a hydroxyl radical, an —SO$_3$M radical, a (C$_1$-C$_6$) aminoalkoxy radical which is optionally substituted on the amine, a (C$_2$-C$_6$) aminoacyl radical which is optionally substituted on the amine, a radical —NHCH$_2$CH$_2$COOM, a radical —N(CH$_2$CH$_2$COOM)$_2$, an aminoalkyl radical which is optionally substituted on the amine and on the alkyl chain, a (C$_2$-C$_{30}$) carboxyacyl radical, a phosphono group which is optionally substituted with one or two substituted aminoalkyl radicals, a radical —CO(CH$_2$)$_d$COOM, —COOHR$^{11}$(CH$_2$)$_d$COOM, —NHCO(CH$_2$)$_d$OH, or —NH$_3$Y, and a phosphate group,
M, identical or different, is chosen from a hydrogen atom, Na, K, Li, NH$_4$ and an organic amine,
$R^{11}$ is chosen from a hydrogen atom and an —SO$_3$M radical,
d is an integer ranging from 1 to 10,
u is an integer ranging from 0 to 20,
w is an integer ranging from 0 to 500,
t is an integer ranging from 0 to 20,
p is an integer ranging from 1 to 50, a is an integer ranging from 0 to 50,
b is an integer ranging from 0 to 50,
the sum (a+b) is greater than or equal to 2,
c is an integer ranging from 0 to 4,
x is an integer ranging from 1 to 100,
Y is a monovalent inorganic or organic anion.

28. A composition according to claim 27, wherein $R^9$ and $R^{10}$, which are identical or different, are methyl radicals.

29. A composition according to claim 27, wherein the silicone is chosen from those of formulae (X) or (XI) wherein:
c is equal to 2 or 3;
$R^6$ is methyl;
$R^8$ is chosen from a methyl radical, a $(C_{12}-C_{22})$ acyl radical and a —$CO(CH_2)_d COOM$ radical;
a is an integer ranging from 2 to 25,
b is equal to 0,
w is an integer ranging from 0 to 100, and
p is an integer ranging from 1 to 20.

30. A composition according to claim 29, wherein a is an integer ranging form 2 to 15.

31. A composition according to claim 1, wherein the polyoxyalkylenated silicone (ii)$_2$ is chosen from compounds having the following formula (XIII):

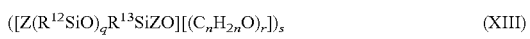

(XIII)

wherein,
$R_{12}$ and $R_{13}$, which are identical or different, are monovalent hydrocarbon radicals,
n is an integer ranging from 2 to 4,
q is an integer greater than or equal to 4,
r is an integer greater than or equal to 4,
s is an integer greater than or equal to 4,
Z is a divalent organic group which is linked to the adjacent silicon atom by a carbon-silicon bond and to a polyoxyalkylene block by an oxygen atom, the average molecular weight of each siloxane block ranging from 400 to 10,000, the average molecular weight of each polyoxyalkylene block ranging from 300 to 10,000, all of the siloxane blocks representing from 10% to 95% by weight of the block copolymer, and the number-average molecular weight of the block copolymer ranging from 2500 to 1,000,000.

32. A composition according to claim 31, wherein q is an integer ranging from 4 to 200.

33. A composition according to claim 31, wherein r is an integer ranging from 4 to 200.

34. A composition according to claim 31, wherein s is an integer ranging from 4 to 1000.

35. A composition according to claim 31, wherein the number-average molecular weight of the block copolymer ranges from 3000 to 200,000.

36. A composition according to claim 1, wherein the at least one silicone (ii) is present in the composition in an amount ranging from 0.01 to 20% by weight relative to the total weight of the composition.

37. A composition according to claim 36, wherein the at least one silicone (ii) is present in the composition in an amount ranging from 0.1 to 10% by weight relative to the total weight of the composition.

38. A composition according to claim 1, wherein said medium suitable for dyeing comprises water or a mixture of water and of at least one organic solvent.

39. A composition according to claim 1, wherein the composition has a pH ranging from 2 to 11.

40. A composition according to claim 39, wherein the composition has a pH ranging from 5 to 10.

41. A composition according to claim 1, further comprising at least one oxidation base chosen from para-phenylenediamines, bis-phenylalkylenediamines, para-aminophenols, ortho-aminophenols, and heterocyclic bases.

42. A composition according to claim 41, wherein said at least one oxidation base is present in an amount ranging from 0.0005 to 12% by weight of the total weight of the composition.

43. A composition according to claim 42, wherein said at least one oxidation base is present in an amount ranging from 0.005 to 6% by weight of the total weight of the composition.

44. A composition according to claim 41, further comprising at least one coupler chosen from meta-phenylenediamines, meta-aminophenols, meta-diphenols, and heterocyclic couplers.

45. A composition according to claim 44, wherein said at least one coupler is present in an amount ranging from 0.0001 to 10% by weight relative to the total weight of the composition.

46. A composition according to claim 45, wherein said at least one coupler is present in an amount ranging from 0.005 to 5% by weight relative to the total weight of the composition.

47. A composition according to claim 1, further comprising at least one oxidizing agent.

48. A method of dyeing keratinous fibers comprising:
applying to the fibers, for a sufficient time to develop the desired coloration, at least one dyeing composition comprising, in a medium suitable for dyeing:
(i) at least one cationic direct dye chosen from: compounds having the following formulae (I), or (III) and:
(ii) at least one silicone;
wherein said at least one cationic direct dye is chosen from:
a) compounds of following formula (I):

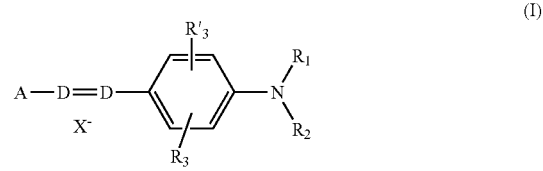

(I)

wherein:
D is a nitrogen atom or a —CH group,
$R_1$ and $R_2$, which are identical or different, are chosen from a hydrogen atom; a $(C_1-C_4)$ alkyl radical which may be unsubstituted or substituted with a —CN radical, an —OH radical or an —$NH_2$ radical or form with each other or with a carbon atom of the benzene ring an optionally oxygen-containing or nitrogen-containing heterocycle which may be unsubstituted or substituted with at least one radical chosen from $(C_1-C_4)$ alkyl radicals; and a 4'-aminophenyl radical,
$R_3$ and $R'_3$, which are identical or different, are chosen from a hydrogen atom; a halogen atom chosen from chlorine, bromine, iodine, and fluorine; a cyano group; a $(C_1-C_4)$ alkyl radical; a $(C_1-C_4)$ alkoxy radical; and a $(C_1-C_4)$ acetyloxy radical, X⁻ is an anion, A is chosen from the following structures A₁ to A₁₉:

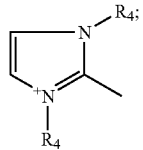

A₁

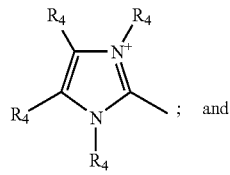

A₇

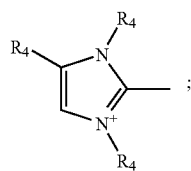

A₁₉ wherein:

$R_4$ is a $(C_1-C_4)$ alkyl radical which may be unsubstituted or substituted with a hydroxyl radical, and $R_5$ is a $(C_1-C_4)$ alkoxy radical;

b) compounds of following formulae (III):

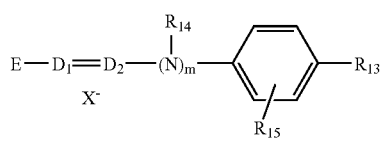

(III)

wherein:

$R_{13}$ is chosen from a hydrogen atom, a $(C_1-C_4)$ alkoxy radical, a halogen atom chosen from bromine, chlorine, iodine and fluoine atoms, and an amino radical, $R_{14}$ is chosen from a hydrogen atom, and a $(C_1-C_4)$ alkyl radical, or forms, with a carbon atom of the benzene ring, a heterocycle which optionally contains an oxygen heteroatom and which is unsubstituted or substituted with at least one radical chosen from $(C_1-C_4)$ alkyl radicals, $R_{15}$ is a hydrogen atom or a halogen atom chosen from bromine, chlorine, iodine and fluorine, $R_{16}$ and $R_{17}$, which are identical or different, are a hydrogen atom or a $(C_1-C_4)$ alkyl radical, $D_1$ and $D_2$, which are identical or different, are a nitrogen atom or a —CH group, m is 0 or 1, with the proviso that when $R_{13}$ is an unsubstituted amino group, then $D_1$ and $D_2$ simultaneously are a —CH group and m=0, X⁻ is an anion, E is a group chosen from the following structures E1, E2 and E7:

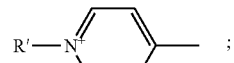

E1

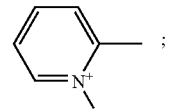

E2

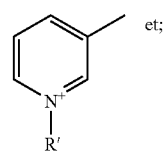

et;

E7 wherein R' is a $(C_1-C_4)$ alkyl radical;

wherein said at least one silicone is chosen from:
(ii)₁—aminated silicones;
(ii)₂—polyoxyalkylenated silicones; and
(ii)₃—silicone gums and resins.

49. A method according to claim 48, wherein the keratinous fibers are human keratinous fibers.

50. A method according to claim 49, wherein the human keratinous fibers are hair.

51. A method according to claim 48, further comprising rinsing said keratinous fibers after applying said composition thereon.

52. A method according to claim 51, further comprising washing said keratinous fibers with a shampoo after said rinsing.

53. A method according to claim 52, further comprising rinsing again said keratinous fibers after said washing.

54. A method according to claim 48, further comprising drying said keratinous fibers.

55. A method for dyeing keratinous fibers, comprising:
separately storing a first composition and a second composition;
mixing said first composition with said second composition before applying the resultant mixture to said keratinous fibers; and
applying said mixture to said keratinous fibers;
wherein said first composition comprises, in a medium suitable for dyeing, at least one cationic direct dye and at least one oxidation base;
wherein said second composition comprises, in a medium suitable for dyeing, at least one oxidizing agent;
wherein either said first composition or said second composition comprises at lease one silicone chosen from:
(ii)₁—aminated silicones;
(ii)₂—polyoxyalkylenated silicones; and
(ii)₃—silicone gums and resins;
wherein said at least one cationic direct dye is chosen from:
a) compounds of following formula (I):

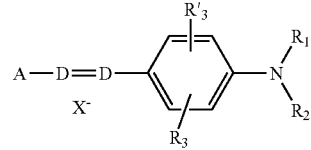

(I)

wherein:
D is a nitrogen atom or a —CH group,
$R_1$ and $R_2$, which are identical or different, are chosen from a hydrogen atom; a $(C_1-C_4)$ alkyl radical which may be unsubstituted or substituted with a —CN radical, an —OH radical or an —NH$_2$ radical or form with each other or with a carbon atom of the benzene ring an optionally oxygen-containing or nitrogen-containing heterocycle which may be unsubtituted or substituted with at least one radical chosen from $(C_1-C_4)$ alkyl radicals; and a 4'-aminophenyl radical,
$R_3$ and $R'_3$, which are identical or different, are chosen from a hydrogen atom; a halogen atom chosen from chlorine, bromine, iodine, and fluorine; a cyano group; a $(C_1-C_4)$ alkyl radical; a $(C_1-C_4)$ alkoxy radical; and a $(C_1-C_4)$ acetyloxy radical,
X⁻ is an anion,
A is chosen from the following structures $A_1$ $A_7$, and $A_{19}$:

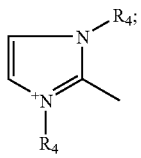

$A_1$

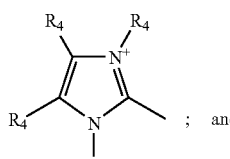

$A_7$

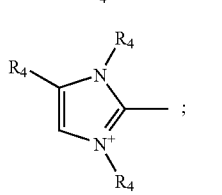

$A_{19}$ wherein:
$R_4$ is a $(C_1-C_4)$ alkyl radical which may be unsubstituted or substituted with a hydroxyl radical, and
$R_5$ is a $(C_1-C_4)$ alkoxy radical; and
b) compounds of following formulae (III):

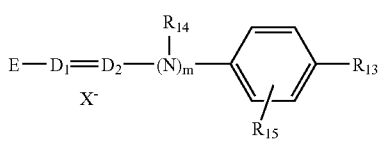

(III)

wherein:
$R_{13}$ is chosen from a hydrogen atom, a $(C_1-C_4)$ alkoxy radical, a halogen atom chosen from bromine, chlorine, iodine and fluoine atoms, and an amino radical,
$R_{14}$ is chosen from a hydrogen atom, and a $(C_1-C_4)$ alkyl radical, or forms, with a carbon atom of the benzene ring, a heterocycle which optionally contains an oxygen heteroatom and which is unsubstituted or substituted with at least one radical chosen from $(C_1-C_4)$ alkyl radicals, $R_{15}$ is a hydrogen atom or a halogen atom chosen from bromine, chlorine, iodine and fluorine,
$R_{16}$ and $R_{17}$, which are identical or different, are a hydrogen atom or a $(C_1-C_4)$ alkyl radical,
$D_1$ and $D_2$, which are identical or different, are a nitrogen atom or a —CH group,
m is 0 or 1,
with the proviso that when $R_{13}$ is an unsubstituted amino group, then $D_1$ and $D_2$ simultaneously are a —CH group and m=0,
X⁻ is an anion,
E is a group chosen from the following structures E1, E2, and E7:

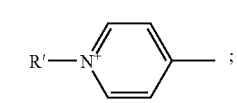

E1

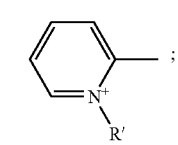

E2

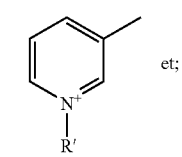

E7 wherein R' is a $(C_1-C_4)$ alkyl radical.

56. A method according to claim 55, wherein the keratinous fibers are human keratinous fibers.

57. A method according to claim 56, wherein the human keratinous fibers are hair.

58. A method for dyeing keratinous fibers, comprising:
separately storing a first composition and a second composition;
mixing said first composition with said second composition before applying the resultant mixture to said keratinous fibers; and
applying said mixture to said keratinous fibers;
wherein said first composition comprises, in a medium suitable for dyeing, at least one cationic direct dye;
wherein said second composition comprises, in a medium suitable for dyeing, at least one oxidizing agent;
wherein either said first composition or said second composition comprises at lease one silicone chosen from:
(ii)$_1$—aminated silicones;
(ii)$_2$—polyoxyalkylenated silicones; and
(ii)$_3$—silicone gums and resins;
wherein said at least one cationic direct dye is chosen from:
a) compounds of following formula (I):

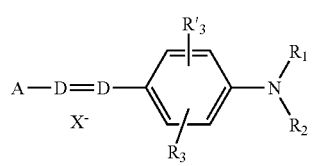

(I)

wherein:
D is a nitrogen atom or a —CH group,
R$_1$ and R$_2$, which are identical or different, are chosen from a hydrogen atom; a (C$_1$-C$_4$) alkyl radical which may be unsubstituted or substituted with a —CN radical, an —OH radical or an —NH$_2$ radical or form with each other or with a carbon atom of the benzene ring an optionally oxygen-containing or nitrogen-containing heterocycle which may be unsubtituted or substituted with at least one radical chosen from (C$_1$-C$_4$) alkyl radicals; and a 4'-aminophenyl radical,
R$_3$ and R'$_3$, which are identical or different, are chosen from a hydrogen atom; a halogen atom chosen from chlorine, bromine, iodine, and fluorine; a cyano group; a (C$_1$-C$_4$) alkyl radical; a (C$_1$-C$_4$) alkoxy radical; and a (C$_1$-C$_4$) acetyloxy radical,
X$^{31}$ is an anion,
A is chosen from the following structures A$_1$, A$_7$, and A$_{19}$:

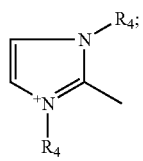   A$_1$

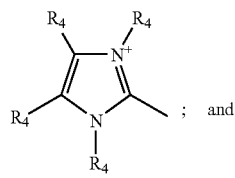   ; and   A$_7$

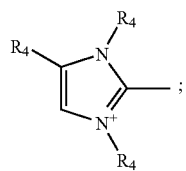   ;   A$_{19}$ wherein:
R$_4$ is a (C$_1$-C$_4$) alkyl radical which may be unsubstituted or substituted with a hydroxyl radical, and
R$_5$ is a (C$_1$-C$_4$) alkoxy radical; and
b) compounds of following formulae (III):

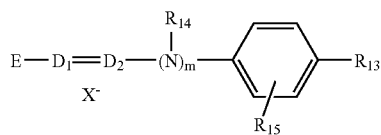   (III)

wherein:
R$_{13}$ is chosen from a hydrogen atom, a (C$_1$-C$_4$) alkoxy radical, a halogen atom chosen from bromine, chlorine, iodine and fluoine atoms, and an amino radical,
R$_{14}$ is chosen from a hydrogen atom, and a (C$_1$-C$_4$) alkyl radical, or forms, with a carbon atom of the benzene ring, a heterocycle which optionally contains an oxygen heteroatom and which is unsubstituted or substituted with at least one radical chosen from (C$_1$-C$_4$) alkyl radicals, R$_{15}$ is a hydrogen atom or a halogen atom chosen from bromine, chlorine, iodine and fluorine,
R$_{16}$ and R$_{17}$, which are identical or different, are a hydrogen atom or a (C$_1$-C$_4$) alkyl radical,
D$_1$ and D$_2$, which are identical or different, are a nitrogen atom or a —CH group,
m is 0 or 1,
with the proviso that when R$_{13}$ is an unsubstituted amino group, then D$_1$ and D$_2$ simultaneously are a —CH group and m=0,
X$^-$ is an anion,
E is a group chosen from the following structures E1, E2, and E7:

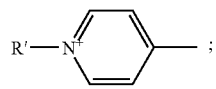   E1

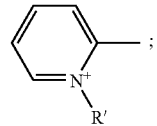   E2

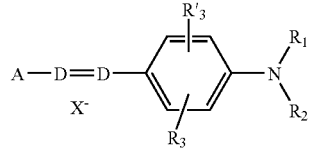   et;   E7 wherein R' is a (C$_1$-C$_4$) alkyl radical.
59. A method according to claim 58, wherein the keratinous fibers are human keratinous fibers.
60. A method according to claim 59, wherein the human keratinous fibers are hair.
61. A multicompartment dyeing kit, comprising a first compartment containing a first composition and a second compartment containing a second composition;
wherein said first composition comprises, in a medium suitable for dyeing, at least one catonic direct dye and at least one oxidation base;
wherein said second composition comprises, in a medium suitable for dyeing, at least one oxidizing agent;
wherein either said first composition or said second composition comprises at least one silicone chosen from:
(ii)$_1$—aminated silicones;
(ii)$_2$—polyoxyalkylenated silicones; and
(ii)$_3$—silicone gums and resins;
wherein said at least one cationic direct dye is chosen from:
a) compounds of following formula (I):

$$A-D=D-\underset{R_3}{\overset{R'_3}{\underset{\phantom{X^-}}{\bigodot}}}-N\underset{R_2}{\overset{R_1}{\diagdown}} \quad X^- \quad (I)$$

wherein:
D is a nitrogen atom or a —CH group,
R$_1$ and R$_2$, which are identical or different, are chosen from a hydrogen atom; a (C$_1$-C$_4$) alkyl radical which may be unsubstituted or substituted with a —CN radical, an —OH radical or an —NH$_2$ radical or form with each other or with a carbon atom of the benzene ring an optionally oxygen-containing or nitrogen-containing heterocycle which may be unsubtituted or substituted with at least one radical chosen from (C$_1$-C$_4$) alkyl radicals; and a 4'-aminophenyl radical, R$_3$ and R'$_3$, which are identical or different, are chosen from a hydrogen atom; a halogen atom chosen from chlorine, bromine, iodine, and fluorine; a cyano group; a (C$_1$-C$_4$) alkyl radical; a (C$_1$-C$_4$) alkoxy radical; and a (C$_1$-C$_4$) acetyloxy radical, X$^-$ is an anion, A is chosen from the following structures A$_1$, A$_7$, and A$_{19}$:

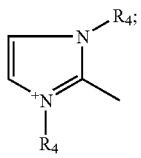

A$_1$

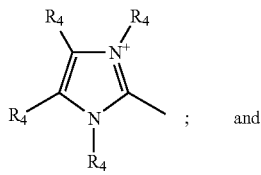

A$_7$

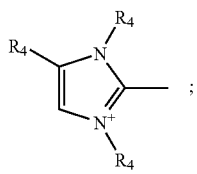

A$_{19}$ wherein:
R$_4$ is a (C$_1$-C$_4$) alkyl radical which may be unsubstituted or substituted with a hydroxyl radical, and
R$_5$ is a (C$_1$-C$_4$) alkoxy radical; and b) compounds of following formulae (III):

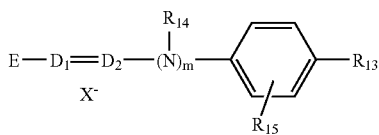

(III)

wherein:
R$_{13}$ is chosen from a hydrogen atom, a (C$_1$-C$_4$) alkoxy radical, a halogen atom chosen from bromine, chlorine, iodine and fluoine atoms, and an amino radical,
R$_{14}$ is chosen from a hydrogen atom, and a (C$_1$-C$_4$) alkyl radical, or forms, with a carbon atom of the benzene ring, a heterocycle which optionally contains an oxygen heteroatom and which is unsubstituted or substituted with at least one radical chosen from (C$_1$-C$_4$) alkyl radicals,
R$_{15}$ is a hydrogen atom or a halogen atom chosen from bromine, chlorine, iodine and fluorine,
R$_{16}$ and R$_{17}$, which are identical or different, are a hydrogen atom or a (C$_1$-C$_4$) alkyl radical, D$_1$ and D$_2$, which are identical or different, are a nitrogen atom or a —CH group,
m is 0 or 1, with the proviso that when R$_{13}$ is an unsubstituted amino group, then D$_1$ and D$_2$ simultaneously are a —CH group and m=0, X$^-$ an anion, E is a group chosen from the following structures E1, E2, and E7:

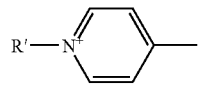

E1

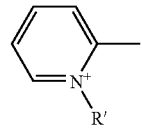

E2

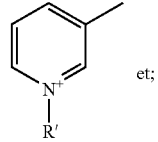

E7 wherein R' is a (C$_1$-C$_4$) alkyl radical.

62. A multicompartment dyeing kit, comprising a first compartment containing a first composition and a second compartment containing a second composition;
wherein said first composition comprises, in a medium suitable for dyeing, at least one cationic direct dye;
wherein said second composition comprises, in a medium suitable for dyeing, at least one oxidizing agent;
wherein either said first composition or said second composition comprises at least one silicone chosen from:
(ii)$_1$—aminated silicones;
(ii)$_2$—polyoxyalkylenated silicones; and
(ii)$_3$—silicone gums and resins;
wherein said at least one cationic direct dye is chosen from:
a) compounds of following formula (I):

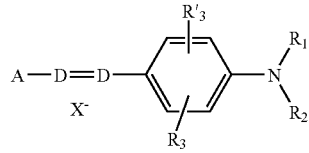

(I)

wherein:
D is a nitrogen atom or a —CH group,
R$_1$ and R$_2$, which are identical or different, are chosen from a hydrogen atom; a (C$_1$-C$_4$) alkyl radical which may be unsubstituted or substituted with a —CN radical, an —OH radical or an —NH$_2$ radical or form with each other or with a carbon atom of the benzene ring an optionally oxygen-containing or nitrogen-containing heterocycle which may be unsubtituted or substituted with at least one radical chosen from (C$_1$-C$_4$) alkyl radicals; and a 4'-aminophenyl radical,
R$_3$ and R'$_3$, which are identical or different, are chosen from a hydrogen atom; a halogen atom chosen from chlorine, bromine, iodine, and fluorine; a cyano group; a $(C_1-C_4)$ alkyl radical; a $(C_1-C_4)$ alkoxy radical; and a $(C_1-C_4)$ acetyloxy radical, $X^-$ an anion, A is chosen from the following structures $A_1$, $A_7$, and $A_{19}$:

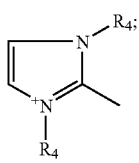
$A_1$

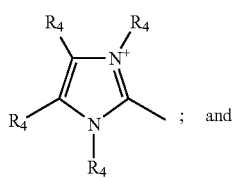
$A_7$ ; and

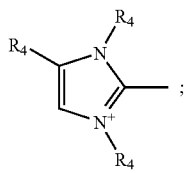
$A_{19}$ ;

wherein:
- $R_4$ is a $(C_1-C_4)$ alkyl radical which may be unsubstituted or substituted with a hydroxyl radical, and
- $R_5$ is a $(C_1-C_4)$ alkoxy radical; and b) compounds of following formulae (III):

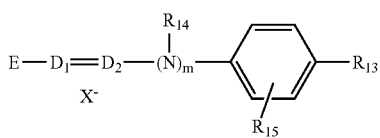
(III)

wherein:
- $R_{13}$ is chosen from a hydrogen atom, a $(C_1-C_4)$ alkoxy radical, a halogen atom chosen from bromine, chlorine, iodine and fluoine atoms, and an amino radical,
- $R_{14}$ is chosen from a hydrogen atom, and a $(C_1-C_4)$ alkyl radical, or forms, with a carbon atom of the benzene ring, a heterocycle which optionally contains an oxygen heteroatom and which is unsubstituted or substituted with at least one radical chosen from $(C_1-C_4)$ alkyl radicals,
- $R_{15}$ is a hydrogen atom or a halogen atom chosen from bromine, chlorine, iodine and fluorine,
- $R_{16}$ and $R_{17}$, which are identical or different, are a hydrogen atom or a $(C_1-C_4)$ alkyl radical,
- $D_1$ and $D_2$, which are identical or different, are a nitrogen atom or a —CH group,
- m is 0 or 1, with the proviso that when $R_{13}$ is an unsubstituted amino group, then $D_1$ and $D_2$ simultaneously are a —CH group and m=0, $X^-$ an anion, E is a group chosen from the following structures E1, E2, and E7:

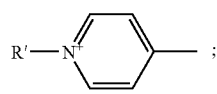
E1

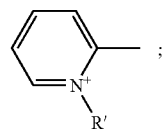
E2

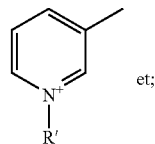
E7
et;

wherein R' is a $(C_1-C_4)$ alkyl radical.

* * * * *

UNITED STATES PATENT AND TRADEMARK OFFICE
CERTIFICATE OF CORRECTION

PATENT NO.       : 7,507,260 B2                                              Page 1 of 7
APPLICATION NO. : 11/539459
DATED            : March 24, 2009
INVENTOR(S)      : Christine Rondeau et al.

It is certified that error appears in the above-identified patent and that said Letters Patent is hereby corrected as shown below:

In claim 1, column 39, line 9, "unsubtituted" should read --unsubstituted--.

In claim 1, column 39, line 48, "formulae" should read --formula--.

In claim 1, column 39, lines 51-55,

" 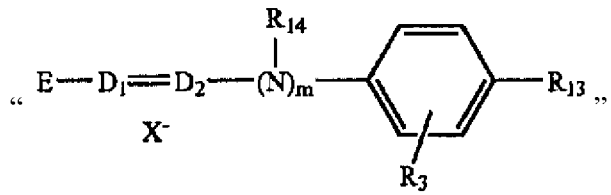 ", should read

-- 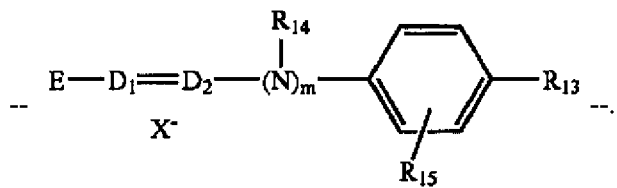 --.

In claim 1, column 40, line 27, following structure E7, delete "et;".

UNITED STATES PATENT AND TRADEMARK OFFICE
CERTIFICATE OF CORRECTION

PATENT NO.         : 7,507,260 B2
APPLICATION NO. : 11/539459
DATED                   : March 24, 2009
INVENTOR(S)         : Christine Rondeau et al.

It is certified that error appears in the above-identified patent and that said Letters Patent is hereby corrected as shown below:

In claim 6, column 42, lines 1-10,

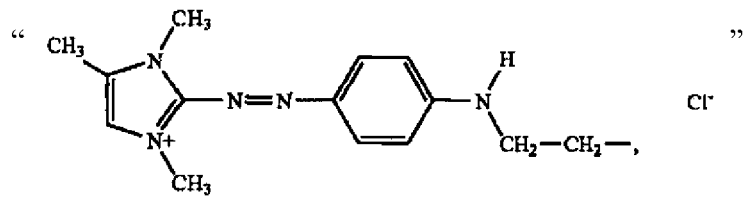

should read

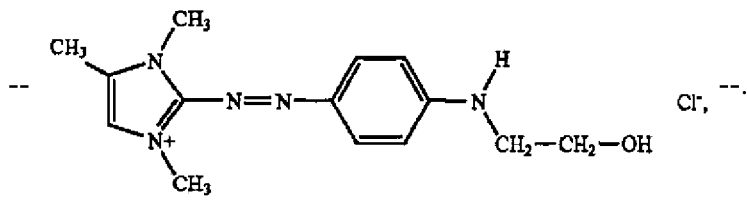

In claim 6, column 42, lines 53-58,

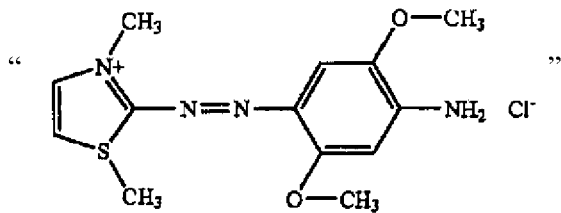

should read

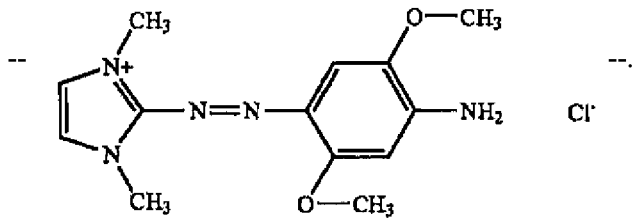

UNITED STATES PATENT AND TRADEMARK OFFICE
CERTIFICATE OF CORRECTION

PATENT NO. : 7,507,260 B2
APPLICATION NO. : 11/539459
DATED : March 24, 2009
INVENTOR(S) : Christine Rondeau et al.

It is certified that error appears in the above-identified patent and that said Letters Patent is hereby corrected as shown below:

In claim 6, column 42, line 56, following structure I51, ", et." should read --.--.

In claim 8, column 44, line 16, following structure III17, "; et." should read --.--

In claim 9, column 44, line 23, "having to the" should read --having the--.

In claim 13, column 45, line 4, "-N-($R^2$)$_2$;" should read -- -N($R^2$)$_2$;--.

In claim 13, column 45, lines 5-6, "-N($R^2$)-$CH_2$-$CH_2$-N$^\square$($R^2$)(H)$_2$Q$^-$," should read -- -N($R^2$)-$CH_2$-$CH_2$-N$^\oplus$-($R^2$)(H)$_2$Q$^-$,--.

In claim 13, column 45, line 7, "$R_2$" should read --$R^2$--.

In claim 21, column 45, lines 27-41,

"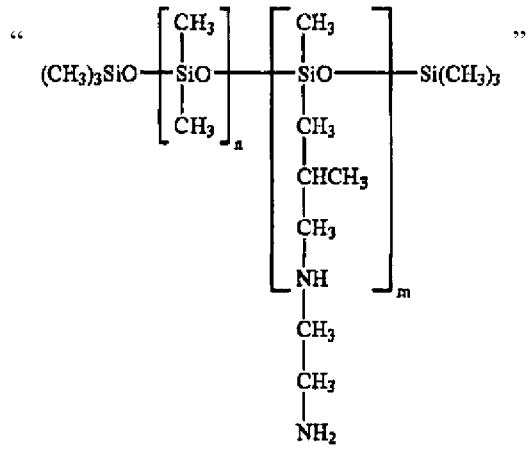"

UNITED STATES PATENT AND TRADEMARK OFFICE
CERTIFICATE OF CORRECTION

PATENT NO. : 7,507,260 B2
APPLICATION NO. : 11/539459
DATED : March 24, 2009
INVENTOR(S) : Christine Rondeau et al.

It is certified that error appears in the above-identified patent and that said Letters Patent is hereby corrected as shown below:

should read

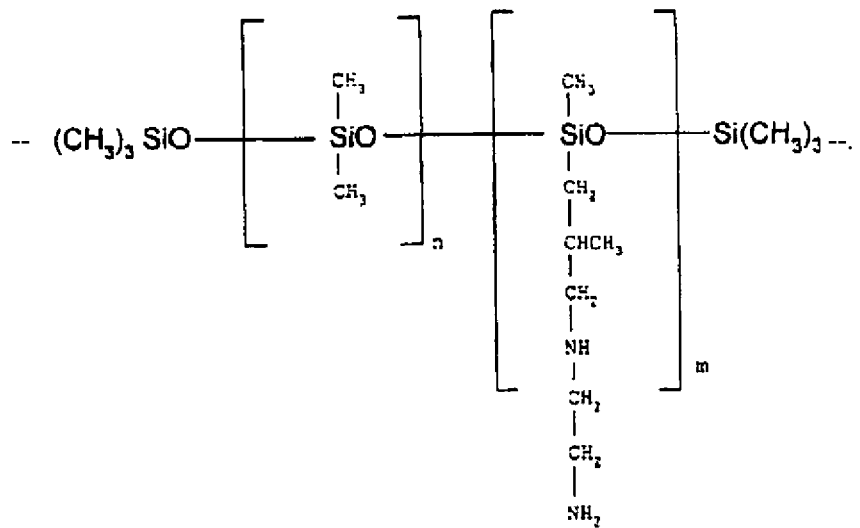

In claim 22, column 45, line 59, "wherein" should read --wherein:--.

In claim 22, column 45, line 63, "$Q^{31}$" should read --$Q^-$--.

In claim 27, column 46, lines 24-28,

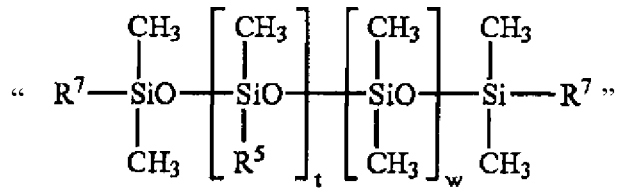

UNITED STATES PATENT AND TRADEMARK OFFICE
CERTIFICATE OF CORRECTION

| | | |
|---|---|---|
| PATENT NO. | : 7,507,260 B2 | Page 5 of 7 |
| APPLICATION NO. | : 11/539459 | |
| DATED | : March 24, 2009 | |
| INVENTOR(S) | : Christine Rondeau et al. | |

It is certified that error appears in the above-identified patent and that said Letters Patent is hereby corrected as shown below:

should read

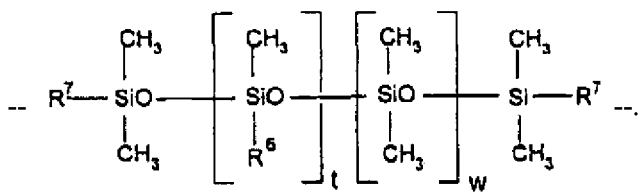

In claim 30, column 47, line 20, "form" should read --from--.

In claim 48, column 48, line 60, "unsubtituted" should read --unsubstituted--.

In claim 48, column 49, line 2, "$A_1$ to $A_{19}$:" should read --$A_1$, $A_7$, and $A_{19}$:--.

In claim 48, column 49, line 34, "formulae" should read --formula--.

In claim 48, column 49, line 48, "fluoine" should read --fluorine--.

In claim 48, column 50, line 16, following structure E7, delete "et;".

In claim 55, column 50, line 55, "lease" should read --least--.

In claim 55, column 51, line 9, "unsubtituted" should read --unsubstituted--.

In claim 55, column 51, line 18, "$A_1$ $A_7$," should read --$A_1$, $A_7$,--.

In claim 55, column 51, line 48, "formulae" should read --formula--.

UNITED STATES PATENT AND TRADEMARK OFFICE
CERTIFICATE OF CORRECTION

PATENT NO. : 7,507,260 B2
APPLICATION NO. : 11/539459
DATED : March 24, 2009
INVENTOR(S) : Christine Rondeau et al.

It is certified that error appears in the above-identified patent and that said Letters Patent is hereby corrected as shown below:

In claim 55, column 51, line 61, "fluoine" should read --fluorine--.

In claim 55, column 52, line 28, following structure E7, delete "et;".

In claim 58, column 52, line 51, "lease" should read --least--.

In claim 58, column 53, line 9, "unsubtituted" should read --unsubstituted--.

In claim 58, column 53, line 17, "$X^{31}$" should read --$X^-$--.

In claim 58, column 53, line 48, "formulae" should read --formula--.

In claim 58, column 53, line 61, "fluoine" should read --fluorine--.

In claim 58, column 54, line 28, following structure E7, delete "et;".

In claim 61, column 54, line 42, "catonic" should read --cationic--.

In claim 61, column 55, line 4, "unsubtituted" should read --unsubstituted--.

In claim 61, column 55, line 43, "formulae" should read --formula--.

In claim 61, column 55, line 57, "fluoine" should read --fluorine--.

UNITED STATES PATENT AND TRADEMARK OFFICE
CERTIFICATE OF CORRECTION

PATENT NO. : 7,507,260 B2
APPLICATION NO. : 11/539459
DATED : March 24, 2009
INVENTOR(S) : Christine Rondeau et al.

It is certified that error appears in the above-identified patent and that said Letters Patent is hereby corrected as shown below:

In claim 61, column 56, line 7, "X⁻ an" should read --X⁻ is an--.

In claim 61, column 56, line 25, following structure E7, delete "et;".

In claim 62, column 56, line 63, "unsubtituted" should read --unsubstituted--.

In claim 62, column 57, line 4, "X⁻ an" should read --X⁻ is an--.

In claim 62, column 57, line 35, "formulae" should read --formula--.

In claim 62, column 58, line 4, "fluoine" should read --fluorine--.

In claim 62, column 58, line 21, "X⁻ an" should read --X⁻ is an--.

In claim 62, column 58, line 38, following structure E7, delete "et;".

Signed and Sealed this

Twelfth Day of May, 2009

JOHN DOLL
*Acting Director of the United States Patent and Trademark Office*